US012708606B2

(12) United States Patent
Xie

(10) Patent No.: US 12,708,606 B2
(45) Date of Patent: Aug. 18, 2026

(54) LITHIUM FLUORIDE NANOPARTICLES FOR THE PROTECTION OF CHONDROCYTES IN OSTEOARTHRITIS

(71) Applicant: UNIVERSITY OF GEORGIA RESEARCH FOUNDATION, INC., Athens, GA (US)

(72) Inventor: Jin Xie, Watkinsville, GA (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/297,365

(22) Filed: Apr. 7, 2023

(65) Prior Publication Data

US 2023/0277472 A1 Sep. 7, 2023

Related U.S. Application Data

(63) Continuation of application No. 16/962,946, filed as application No. PCT/US2019/014132 on Jan. 18, 2019, now abandoned.

(60) Provisional application No. 62/619,512, filed on Jan. 19, 2018.

(51) Int. Cl.

| | |
|---|---|
| ***A61K 9/00*** | (2006.01) |
| ***A61K 9/51*** | (2006.01) |
| ***A61P 19/02*** | (2006.01) |
| *B82Y 5/00* | (2011.01) |

(52) U.S. Cl.

CPC .......... *A61K 9/5115* (2013.01); *A61K 9/0024* (2013.01); *A61K 9/5146* (2013.01); *A61K 9/5161* (2013.01); *A61P 19/02* (2018.01); *B82Y 5/00* (2013.01)

(58) Field of Classification Search

CPC .................................................... A61K 9/5115

See application file for complete search history.

(56) References Cited

U.S. PATENT DOCUMENTS

| | | | | |
|---|---|---|---|---|
| 3,610,795 | A | 10/1971 | Antoine | |
| 6,379,893 | B1 | 4/2002 | Campbell et al. | |
| 2006/0039997 | A1 | 2/2006 | Valducci et al. | |
| 2011/0094416 | A1* | 4/2011 | Kawai | C09C 3/12 204/157.43 |
| 2012/0258172 | A1 | 10/2012 | Khan | |
| 2015/0010063 | A1* | 1/2015 | Komiya | H04N 19/124 375/240.03 |

(Continued)

FOREIGN PATENT DOCUMENTS

| | | |
|---|---|---|
| CN | 105749288 | 7/2016 |

OTHER PUBLICATIONS

Minashima, Lithium Protects Against Cartilage Degradation in Osteoarthritis, Arthritis & Rheumatology, vol. 66, No. 5, May 2014, pp. 1228-1236 (Year: 2014).*

(Continued)

*Primary Examiner* — Paul W Dickinson

(74) *Attorney, Agent, or Firm* — Meunier Carlin & Curfman LLC

(57) ABSTRACT

Disclosed are particles comprising lithium salts and methods for their use in treating inflammatory conditions.

15 Claims, 11 Drawing Sheets

Figure 1E:
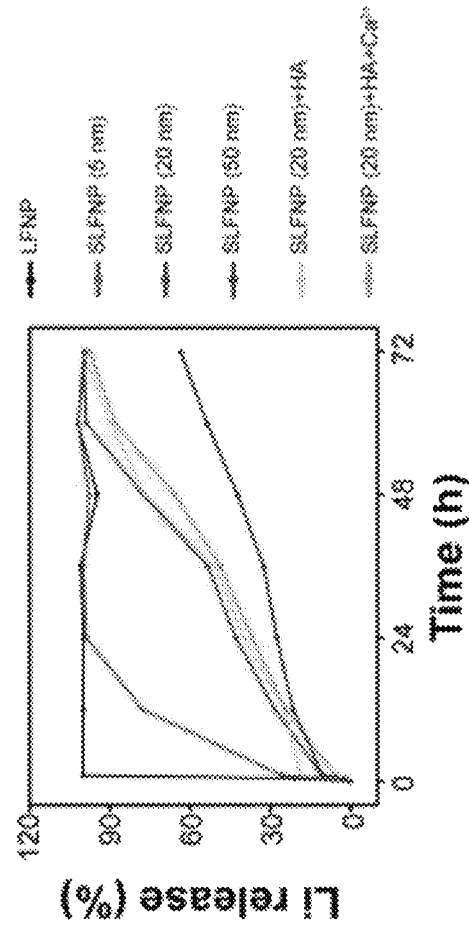

Specification includes a Sequence Listing.

(56) References Cited

U.S. PATENT DOCUMENTS

2015/0045413 A1 2/2015 De Visser
2016/0038641 A1 2/2016 Cashman

OTHER PUBLICATIONS

Hosseini, Improving lithium carbonate therapeutics by pegylated liposomal technology: an in vivo study, Comp Clin Patho, 2016, 25: 211-218 (Year: 2016).*
Todd, Ion Delivery Using Alkalki Halide Nanoparticles for Tumor Therapy and Osteoarthritis Treatment, University of Georgia, 2016, p. 1-97 (Year: 2016).*
Almalik, A. et al. Hyaluronic acid (HA) presentation as a tool to modulate and control the receptor-mediated uptake of HA-coated nanoparticles. Biomaterials 34, 5369-5380 (2013).
Altman, R., Manjoo, A., Fierlinger, A., Niazi, F. & Nicholls, M. The mechanism of action for hyaluronic acid treatment in the osteoarthritic knee: a systematic review. BMC Musculoskelet. Disord. 16, 321 (2015).
Brown, T., Laurent, U. & Fraser, J. Turnover of hyaluronan in synovial joints: elimination of labelled hyaluronan from the knee joint of the rabbit. Exp. Physiol. 76, 125-134 (1991).
Chevalier, X. et al. Tissue inhibitor of metalloprotease-1 (TIMP-1) serum level may predict progression of hip osteoarthritis. Osteoarthritis Cartilage 9, 300-307 (2001).
Cox, S. et al. Collagen degradation by interleukin-1ß-stimulated gingival fibroblasts is accompanied by release and activation of multiple matrix metalloproteinases and cysteine proteinases. Oral Diseases 12, 34-40 (2006).
Finley, P. R., Warner, M. D. & Peabody, C. A. Clinical relevance of drug-interactions with lithium. Clin. Pharmacokinet. 29, 172-191 (1995).
Geddes, J.R et al. Long-term lithium therapy for bipolar disorder: Systematic review and meta-analysis of randomized controlled trials. Am. J. Psychiat. 161, 1517-1517 (2004).
Goldring, M. B. & Otero, M. Inflammation in osteoarthritis. Curr. Opin. Rheumatol. 23, 471-478 (2011).
Hui, W. et al. Lithium protects cartilage from cytokine-mediated degradation by reducing collagen-degrading MMP production via inhibition of the P38 mitogen-activated protein kinase pathway. Rheumatology 49, 2043-2053 (2010).
Hunter, D. J., Neogi, T. & Hochberg, M. C. Quality of osteoarthritis management and the need for reform in the US. Arthrit. Care Res. 63, 31-38 (2011).
LaVan, D. A., McGuire, T. & Langer, R. Small-scale systems for in vivo drug delivery. Nature Biotechnol. 21, 1184-1191 (2003).
Lawrence, R. C. et al. Estimates of the prevalence of arthritis and other rheumatic conditions in the United States. Arthritis Rheum. 58, 26-35 (2008).
Lewis, A. L. & Illum, L. Formulation strategies for sustained release of proteins. Therapeutic Delivery 1, 457-479 (2010).
Marmol, F. Lithium: Bipolar disorder and neurodegenerative diseases Possible cellular mechanisms of the therapeutic effects of lithium. Prog. Neuro-Psychoph. 32, 1761-1771 (2008).
Marshall, K. & Chan, A. Arthroscopic anterior cruciate ligament transection induces canine osteoarthritis. J. Rheumatol. 23, 338-343 (1996). Abstract.
Martel-Pelletier, J. et al. Neutral proteases capable of proteoglycan digesting activity in osteoarthritic and normal human articular cartilage. Arthritis Rheum. 27, 305-312 (1984).
Minashima, T., Zhang, Y., Lee, Y. & Kirsch, T. Lithium protects against cartilage degradation in osteoarthritis. Arthritis Rheumatol. 66, 1228-1236 (2014).
Oruch, R., Elderbi, M. A., Khattab, H. A., Pryme, I. F. & Lund, A. Lithium: A review of pharmacology, clinical uses, and toxicity. Eur. J. Pharmacol. 740, 464-473 (2014).
Pritzker, K.P. et al. Osteoarthritis cartilage histopathology: grading and staging. Osteoarthritis Cartilage. 14, 13-29 (2006).
Schaafsma, G. Calcium in extracellular fluid: homeostasis. in Calcium in Human Biology, 241-259 (Springer, 1988).
Thompson, C. L. et al. Lithium chloride prevents interleukin-1 induced cartilage degradation and loss of mechanical properties. J. Orthop. Res. 33, 1552-1559 (2015).
Thompson, C. L., Wiles, A., Poole, C. A. & Knight, M. M. Lithium chloride modulates chondrocyte primary cilia and inhibits Hedgehog signaling. Faseb J. 30, 716-726 (2016).
Timmer, R. T. & Sands, J. M. Lithium intoxication. J. Am. Soc. Nephrol. 10, 666-674 (1999).
Young, W. Review of lithium effects on brain and blood. Cell Transplant. 18, 951-975 (2009).
Senter, Peter D., et al. "Generation of 5-fluorouracil from 5-fluorocytosine by monoclonal antibody-cytosine deaminase conjugates." Bioconjugate chemistry 2.6 (1991): 447-451.
Bagshawe, K. D. "Towards generating cytotoxic agents at cancer sites. The First Bagshawe Lecture." Br. J. Cancer 60 (1989): 275-281.
Bagshawe, K. D., et al. "A cytotoxic agent can be generated selectively at cancer sites." British journal of cancer 58.6 (1988): 700-703.
Senter, Peter D., et al. "Generation of cytotoxic agents by targeted enzymes." Bioconjugate chemistry 4.1 (1993): 3-9.
Battelli, M. G., et al. "T lymphocyte killing by a xanthine-oxidase-containing immunotoxin." Cancer Immunology, Immunotherapy 35.6 (1992): 421-425.
Pietersz, Geoffrey A., and Ian FC McKenzie. "Antibody conjugates for the treatment of cancer." Immunological reviews 129.1 (1992): 57-80.
Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.
Hughes, Brenda J., et al. "Monoclonal antibody targeting of liposomes to mouse lung in vivo." Cancer research 49.22 (1989): 6214-6220.
Litzinger and Huang, Biochimica et Biophysica Acta, 1104:179-187, (1992).
Brown and Greene, DNA and Cell Biology 10:6, 399-409 (1991).
Ferrone et al., eds., Noges Publications, Park Ridge, N.J., (1985) ch. 22 and pp. 303-357.
Smith et al., Antibodies in Human Diagnosis and Therapy, Haber et al., eds., Raven Press, New York (1977) pp. 365-389.
Esser, AK et al. "Loss of LARGE2 disrupts functional glycosylation of α-dystroglycan in prostate cancer." (2013) J Biol Chem 288: 2132-2142.
de Bernabe, DB et al. "Loss of alpha-dystroglycan laminin binding in epithelium-derived cancers is caused by silencing of LARGE. " (2009) J Biol Chem 284: 11279-11284.
Singh, J et al. Proteolytic enzymes and altered glycosylation modulate dystroglycan function in carcinoma cells. (2004) Cancer Res. 34: 6152-6159.
Muschler, J et al. "A role for dystroglycan in epithelial polarization: loss of function in breast tumor cells." (2002) Cancer Res. 62: 7102-7109.
Henry, MD et al. "Reduced expression of dystroglycan in breast and prostate cancer" (2001) Hum Pathol 32: 791-795.
International Preliminary Report on Patentability issued for Application No. PCT/US2019/014132, dated Jul. 30, 2020.
Todd, T., et al. " Ion delivery using alkali halide nanoparticles for tumor therapy and osteoarthritis treatment," Dissertation, 2016. 110 pages.
Database Biosis [Online] Biosciences Information Service, Philadelphia, Pa, US; Mar. 13, 2016 (Mar. 13, 2016), Todd Trever et al: "Lithium fluoride nanoparticles injected with hyaluronic acid for management of osteoarthritis pain", Database accession No. PREV201800484499 ; & Abstracts of Papers American Chemical Society, vol. 251, Mar. 13, 2016 (Mar. 13, 2016), 251 St National Meeting and Exposition of the American Chemical Society (ACS); San Diego, CA, USA; Mar. 13-17, 2016.
Extended European Search Report issued in corresponding application No. EP19740871.9, dated Oct. 6, 2021, 9 pages.

(56) References Cited

OTHER PUBLICATIONS

International Search Report and Written Opinion issued in corresponding application No. PCT/US2019/014132, dated May 14, 2019, 11 pages.
Todd et al. Publication Embargo, 2016.

* cited by examiner

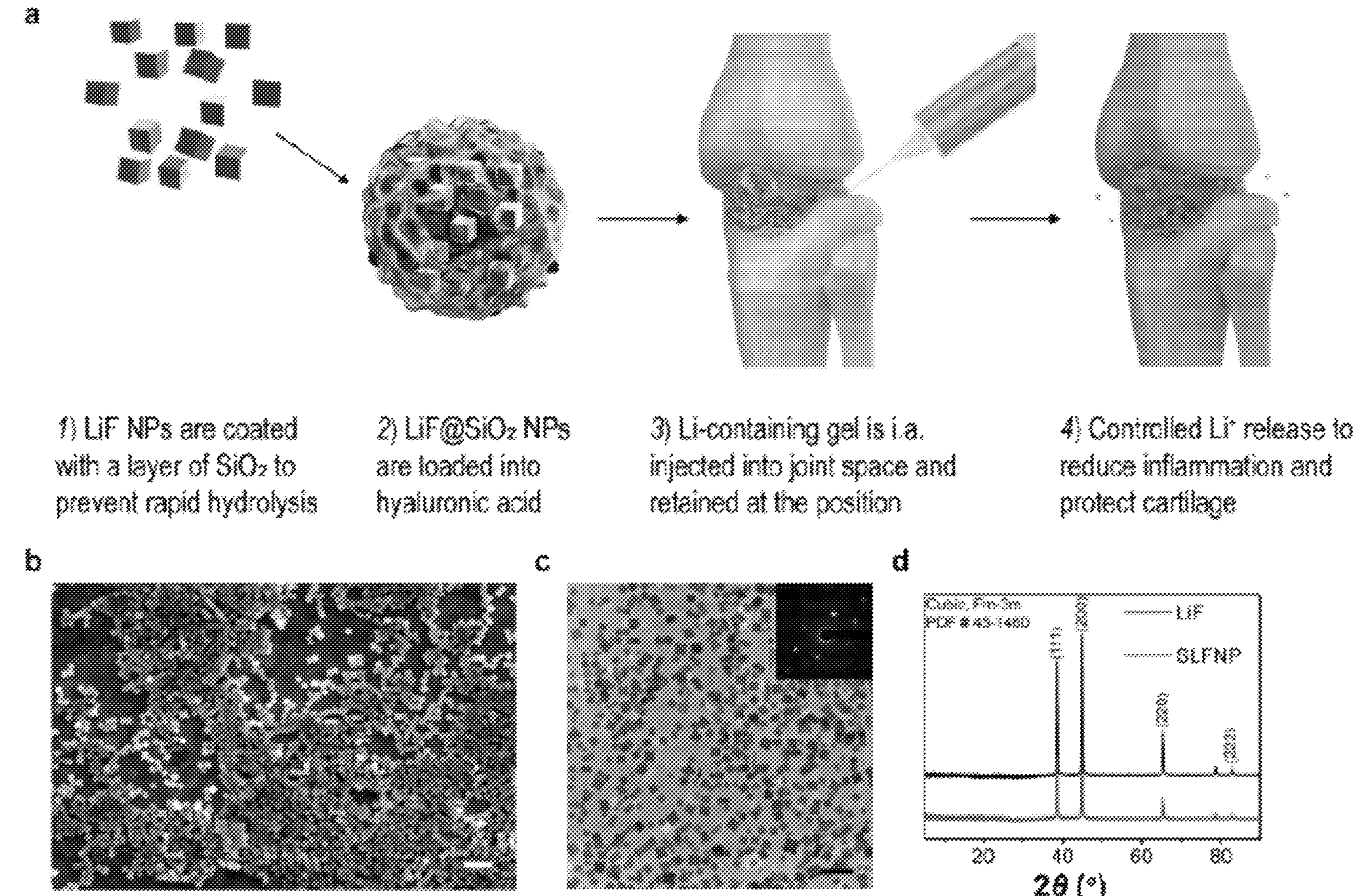
FIG. 1A, FIG. 1B, FIG. 1C, and FIG. 1D f e

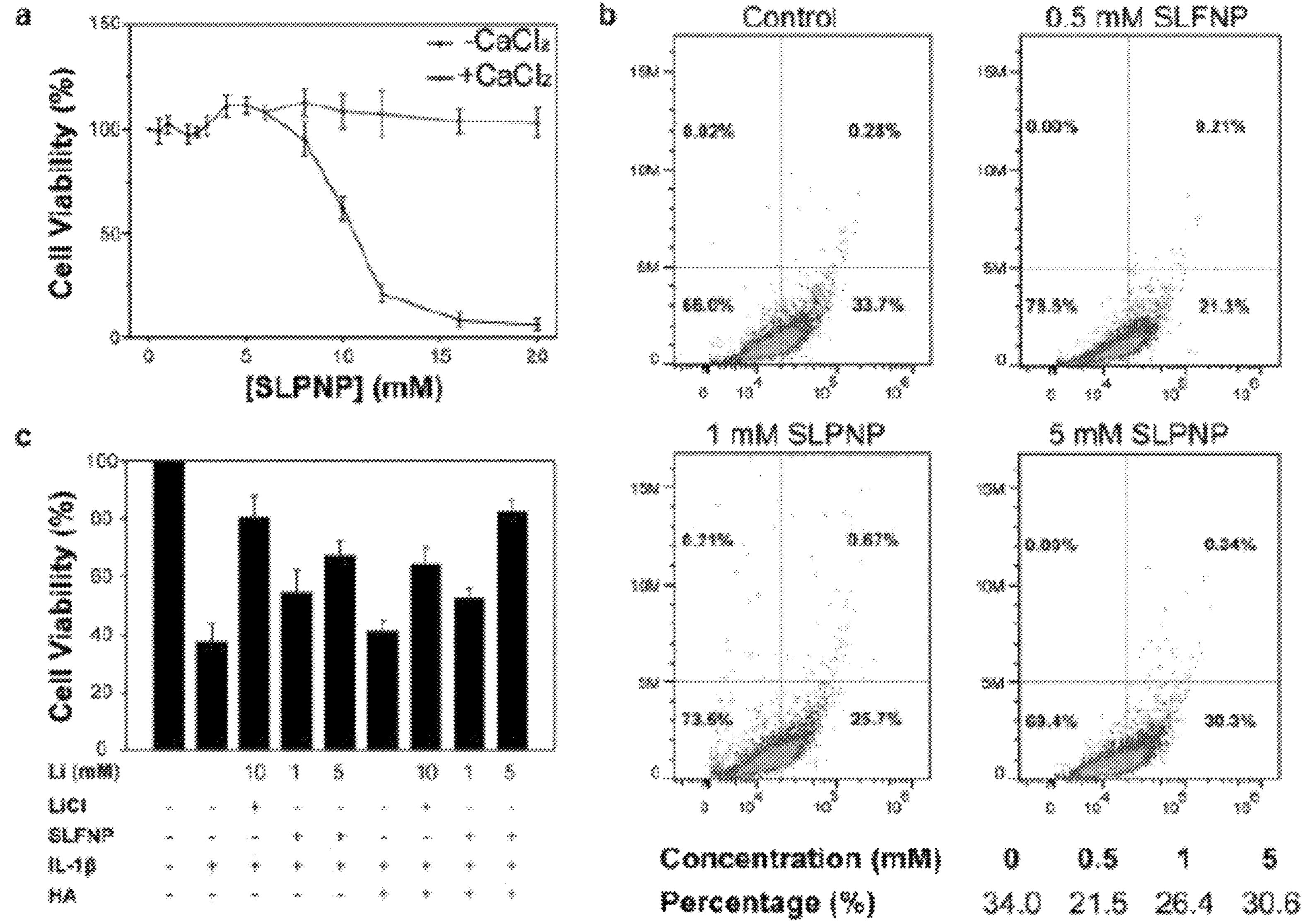
FIG. 3A, FIG. 3B, and FIG. 3C

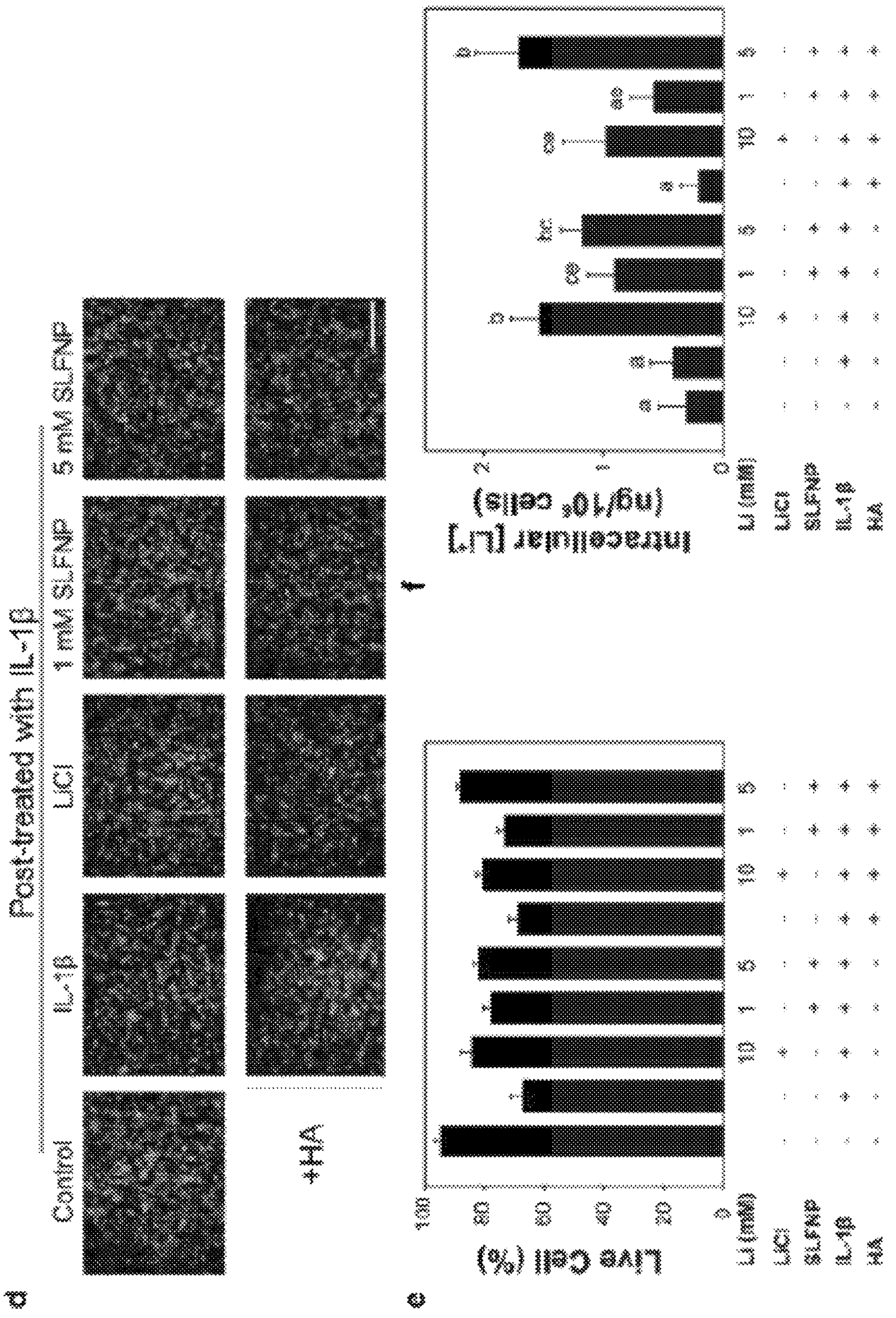
FIG. 3D, FIG. 3E, and FIG. 3F

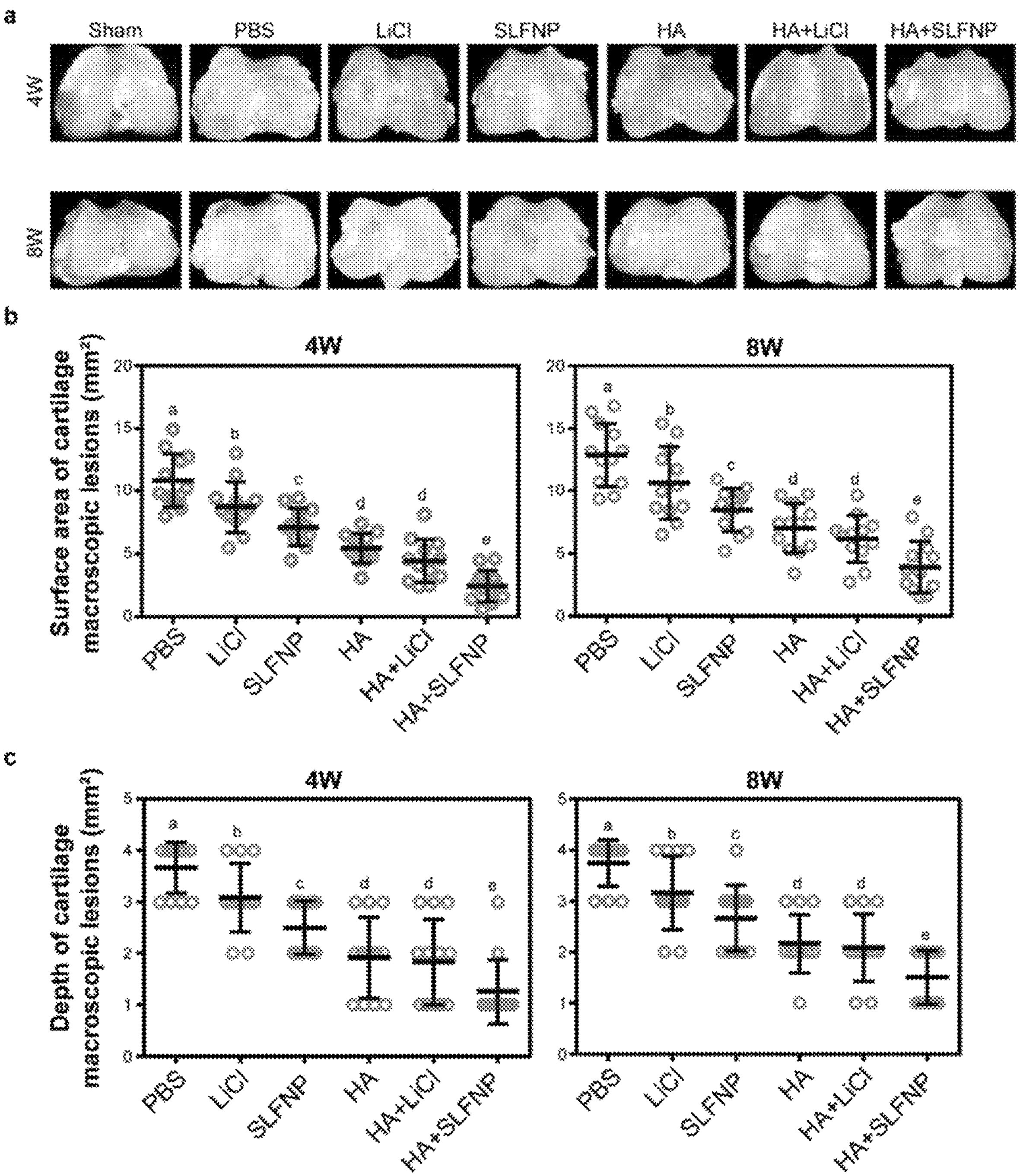
FIG. 5A, FIG. 5B, and FIG. 5C

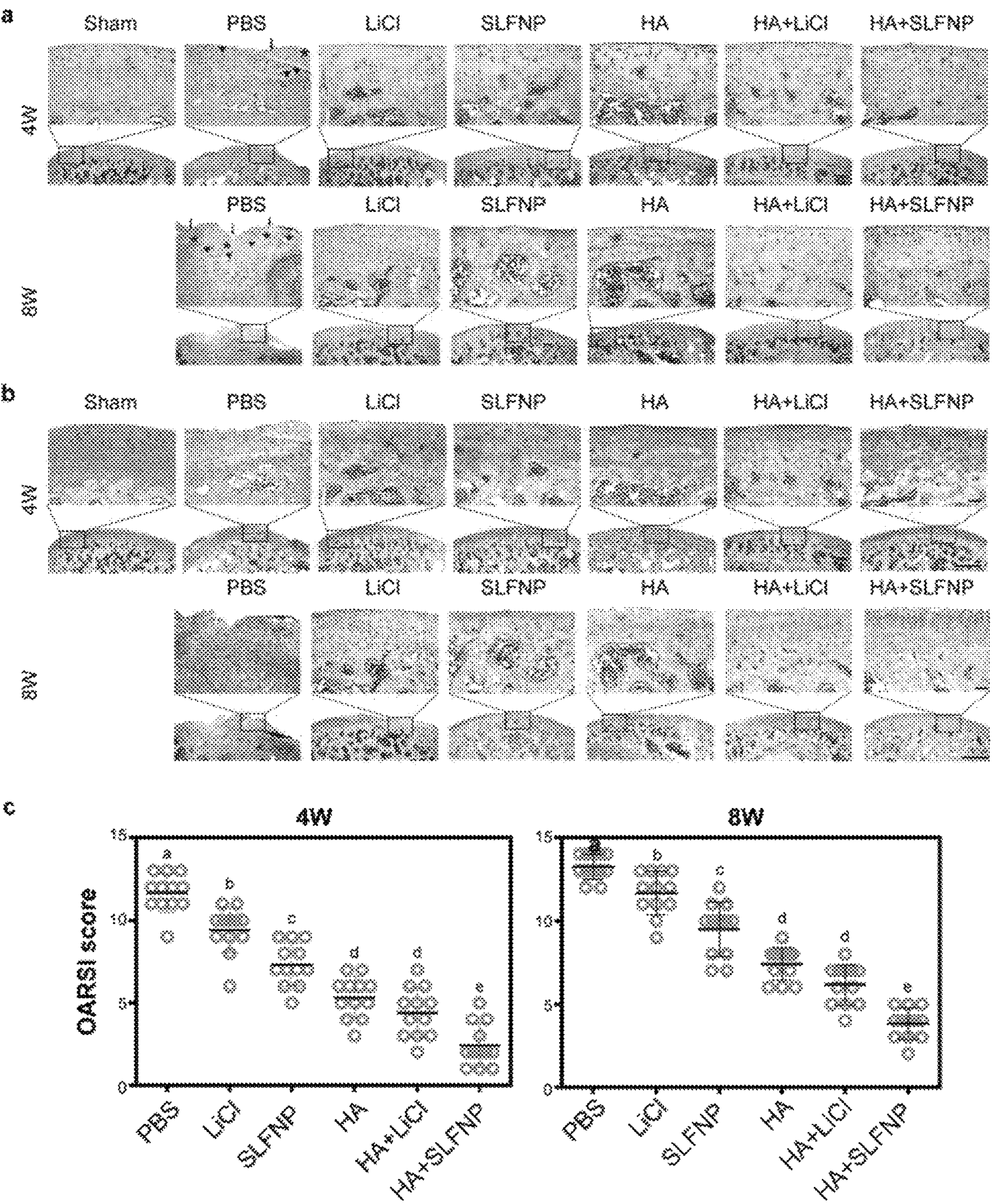
FIG. 6A, FIG. 6B, and FIG. 6C

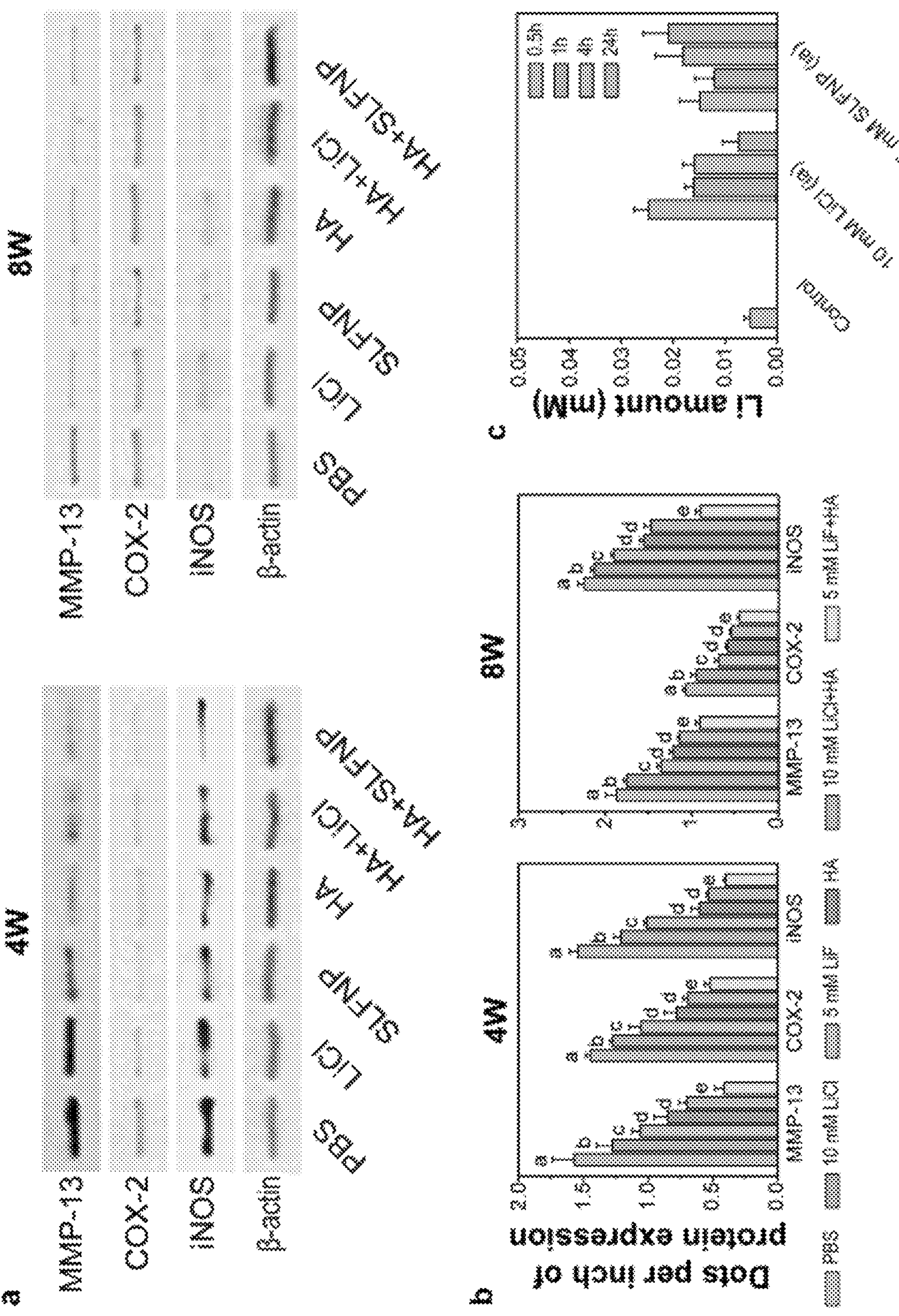
FIG. 7A, FIG. 7B, and FIG. 7C

SEQUENCE LISTING

```
Sequence total quantity: 20
SEQ ID NO: 1            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 1
cacttcacaa gtcggaggct                                              20

SEQ ID NO: 2            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 2
tctgacagtg catcatcgct                                              20

SEQ ID NO: 3            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 3
cccaaatacg caggtgtcct                                              20

SEQ ID NO: 4            moltype = DNA  length = 20
FEATURE                 Location/Qualifiers
misc_feature            1..20
                        note = Synthetic construct
source                  1..20
                        mol_type = other DNA
```

```
                        organism = synthetic construct
SEQUENCE: 4
acacacggag ttgctgtagg                                          20

SEQ ID NO: 5            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 5
gatgacgagc gactgttcca                                          20

SEQ ID NO: 6            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 6
caatgttgaa ggtgtccggc                                          20

SEQ ID NO: 7            moltype = DNA  length = 22
FEATURE                 Location/Qualifiers
misc_feature            1..22
                        note = Synthetic construct
source                  1..22
                        mol_type = other DNA
                        organism = synthetic construct
SEQUENCE: 7
gcttgggtct tgttagccta gt                                       22

SEQ ID NO: 8            moltype = DNA  length = 21
FEATURE                 Location/Qualifiers
misc_feature            1..21
                        note = Synthetic construct
source                  1..21
                        mol_type = other DNA
                        organism = synthetic construct
SEQUENCE: 8
attctgtgca gtcccagtga g                                        21

SEQ ID NO: 9            moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 9
ggctgtgtgc tcatcctacc                                          20

SEQ ID NO: 10           moltype = DNA  length = 21
FEATURE                 Location/Qualifiers
misc_feature            1..21
                        note = Synthetic construct
source                  1..21
                        mol_type = other DNA
                        organism = synthetic construct
SEQUENCE: 10
tggaaaggta ctgaagccac c                                        21

SEQ ID NO: 11           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 11
ggatccatga tggcactgct                                          20

SEQ ID NO: 12           moltype = DNA  length = 20
FEATURE                 Location/Qualifiers
misc_feature            1..20
                        note = Synthetic construct
source                  1..20
```

```
                        mol_type = other DNA
                        organism = synthetic construct
SEQUENCE: 12
tggcttttgc cagtgtaggt                                                20

SEQ ID NO: 13           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 13
gctttctgca actcggacct                                                20

SEQ ID NO: 14           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 14
tctccatggc tggggtgtag                                                20

SEQ ID NO: 15           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 15
ccgctggtct gatggacact                                                20

SEQ ID NO: 16           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 16
aggtgttggg gtctgtgcaa                                                20

SEQ ID NO: 17           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 17
ctggtccttc cggccctaga                                                20

SEQ ID NO: 18           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 18
ggatcggggc ccttctctct                                                20

SEQ ID NO: 19           moltype = DNA  length = 20
FEATURE                 Location/Qualifiers
misc_feature            1..20
                        note = Synthetic construct
source                  1..20
                        mol_type = other DNA
                        organism = synthetic construct
SEQUENCE: 19
cccatctatg agggttacgc                                                20

SEQ ID NO: 20           moltype = DNA  length = 21
FEATURE                 Location/Qualifiers
misc_feature            1..21
                        note = Synthetic construct
```

-continued

```
source                 1..21
                       mol_type = other DNA
                       organism = synthetic construct
SEQUENCE: 20
tttaatgtca cgcacgattt c                                    21
```

LITHIUM FLUORIDE NANOPARTICLES FOR THE PROTECTION OF CHONDROCYTES IN OSTEOARTHRITIS

CROSS-REFERENCE TO RELATED APPLICATION

This application is a continuation of U.S. application Ser. No. 16/962,946, filed on Jul. 17, 2020, which is a national stage application filed under 35 U.S.C. § 371 of PCT/US2019/014132 filed Jan. 18, 2019, which claims the benefit of U.S. Provisional Application No. 62/619,512, entitled "LITHIUM FLUORIDE NANOPARTICLES FOR THE PROTECTION OF CHONDROCYTES IN OSTEOARTHRITIS," filed Jan. 19, 2018, the disclosures of which are incorporated herein by reference in their entireties.

This invention was made with government support under Grant No. R01EB022596 and R01NS093314 awarded by the National Institutes of Health and NSF1552617 awarded by the National Science Foundation. The government has certain rights in the invention.

REFERENCE TO SEQUENCE LISTING

The sequence listing submitted on Apr. 7, 2023, as an .XML file entitled "10067-042US2.XML" created on Apr. 7, 2023, and having a file size of 26,372 bytes is hereby incorporated by reference pursuant to 37 C.F.R. § 1.52(e)(5).

I. BACKGROUND

Osteoarthritis (OA) affects more than 27 million people in the U.S. and its prevalence is on the rise due to an aging population and an increased prevalence of obesity. OA is characterized by abnormality and disruption of articular cartilage, especially in joints with load bearing functions, such as the knees. This causes pain, swelling, stiffness, and a reduced ability to rise, stand, and walk. Currently, OA has no cure. The clinical treatment options, including COX-2 inhibitors, nonsteroidal anti-inflammatory drugs (NSAIDS), hyaluronic acid (HA), and steroids, aim to relieve the symptoms rather than altering the course of disease progression. When these non-surgical managements are no longer sufficient, joint replacement surgery is the main treatment option. Hence, there remains a critical need for new and effective treatments for OA.

While conventionally regarded as a non-inflammatory disease, accumulating evidence implicates inflammation in OA advancement, and there is a growing interest in exploiting anti-inflammatory treatments to reverse or slow OA progression. One promising therapeutic is lithium. Although possessing a long clinical history for treatment of bipolar disorder, the administration of lithium is problematic. For bipolar disorder treatment, lithium salts are taken orally, and the serum lithium concentration is maintained below 1.5 mM to avoid systemic toxicities such as diarrhea, muscular weakness, blurred vision, coma, and even death. On the other hand, in vitro studies show that a much higher local lithium concentration is needed for effective anti-collagenolytic and anti-gelatinolytic activities (e.g. 5-10 mM). What is needed is an implantable drug delivery system that permits controlled release of lithium at therapeutically effective concentrations while avoiding systemic toxicities.

II. SUMMARY

Disclosed are methods and compositions related to particles comprising a lithium core (for example a lithium core comprising a therapeutically effective concentration of a lithium salt) and an encapsulating shell.

Also disclosed herein are particles of any preceding aspect, wherein the encapsulating shell comprises a silica shell, such as, for example a Tetraethyl orthosilicate shell. In one aspect, the thickness of the silica shell is at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75, nm.

In one aspect, disclosed herein are particles of any preceding aspect, wherein the lithium salt of the lithium salt core is selected from the group consisting of lithium fluoride (LiF) salt, lithium bromide (LiBr) salt, lithium chloride (LiCl) salt, lithium iodide (LiI) salt, lithium aluminum oxide ($LiALO_2$) salt, Lithium carbonate ($LiCO_3$) salt, Lithium phosphate ($Li_3PO_4$) salt, and lithium tantalum oxide ($LiTaO_3$) salt.

Also disclosed herein are particles of any preceding aspect, wherein the concentration of Li salt (such as, for example a LiF salt) comprises 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30 mM.

In one aspect, disclosed herein are particles of any preceding aspect, wherein the lithium core further comprises an eluting matrix; that releases the lithium salt (such as, for example, a LiF salt) from the matrix over a sustained rate.

Also disclosed are particles of any preceding aspect, wherein the eluting matrix comprises hyaluronic acid.

In one aspect, disclosed herein are particles of any preceding aspect, wherein the lithium core is synthesized in a synthesis matrix Also disclosed herein are particles of any preceding aspect, wherein the synthesis matrix comprises a mixture of polyethylene glycol:ethylene glycol.

In one aspect, disclosed herein are particles of any preceding aspect, wherein the synthesis matrix comprises a 0.5:1, 0.6:1, 0.7:1, 0.8:1, 0.9:1, 1:1, 1.1:1, 1.2:1, 1.3:1 1.4:1, 1.5:1, 1.6:1, 1.7:1, 1.8:1, 1.9:1, 2:1, 2.5:1, 3:1, 4:1, or 5:1 ratio of polyethylene glycol:ethylene glycol, or pure glycol, pure ethylene, ethanol, methanol, acetone, dimethylsulfoxide, polyvinylpyrrolidone (PVP), poly(acrylic acid) (PAA), polyethylenimine (PEI), and dimethylformamide Also disclosed herein are particles of any preceding aspect, wherein the size of the lithium core is 20, 25, 30, 35, 40, 45, 50, 55, 60, 65, 70, 75, 80, 85, 90, 95, 100, 105, 110, 115, 120, 125, 130, 135, 140, 145, or 150 nm.

In one aspect, disclosed herein are pharmaceutical compositions comprising the particle of any preceding aspect.

Also disclosed herein are pharmaceutical compositions of any preceding aspect, further comprising hyaluronic acid (HA), such as, an HA hydrogel.

In one aspect, disclosed herein are methods of treating an inflammatory condition (such as, for example, osteoarthritis) in a subject comprising administering to the subject the particle or pharmaceutical composition of any preceding aspect.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 1F:
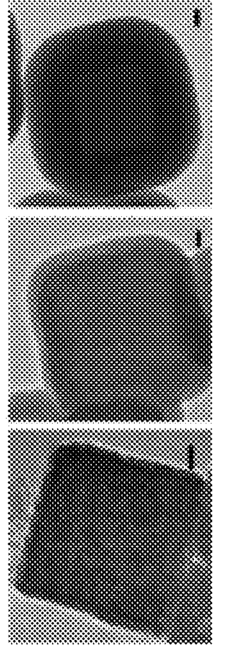

FIGS. 1A, 1B, 1C, 1D, 1E, and 1F show the synthesis and characterization of LiF nanoparticles. FIG. 1A shows a general schematic for the implementation of SLFNP. LiF nanoparticles were coated with a layer of SiO2 and incorporated into a HA gel matrix. The matrix was then injected into an osteoarthritic induced joint where the sustained release of lithium and the viscosupplementation effect of HA reduce inflammation and arthritic destruction. FIG. 1B shows SEM image of LiF nanoparticles. Inlet: SAED analysis. Scale bar: 500 nm. FIG. 1C shows TEM image of LiF nanoparticles. Scale bar: 500 nm. FIG. 1D shows XRD pattern of LiF nanoparticles and SLFNP. FIG. 1E shows TEM images of SLFNP with 5, 20, and 50 nm silica coating. Scale bar: 20 nm. FIG. 1F shows Lithium release curves with different nanoparticles. These include SLFNP with 5, 20, and 50 nm silica coating. For SLFNP with 20-nm silica coating, the release studies were also performed with SLFNP+HA, with and without supplementing the incubation medium with 1.5 mM $Ca^{2+}$.

Figure 2:
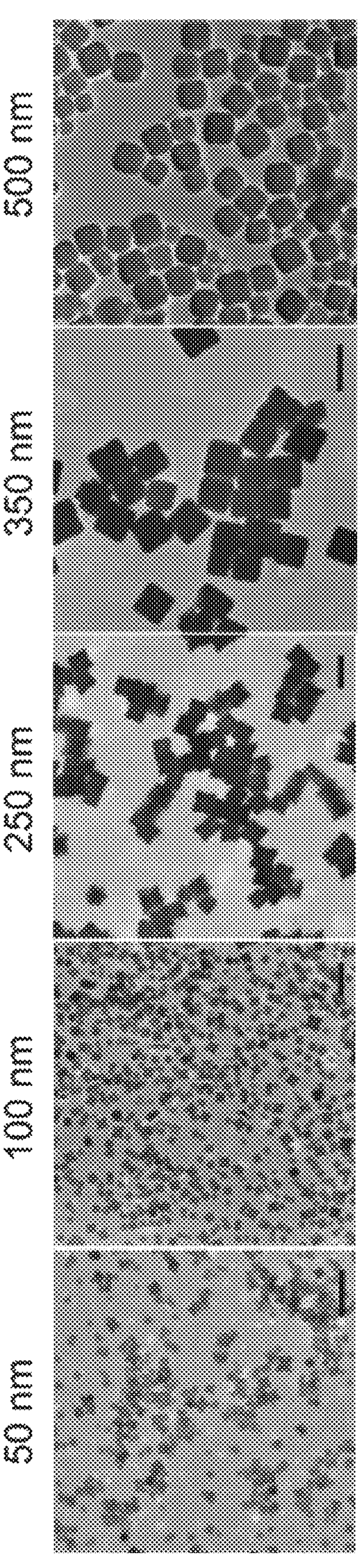

FIG. 2 shows TEM images of LiF nanoparticles of different sizes. Scale bars, 500 nm.

FIGS. 3A, 3B, 3C, 3D, 3E, and 3F show the impact of SLFNP on chondrocyte viability and proliferation. FIG. 3A shows sell viability, assessed by CCK-8 assay. SLFNP were incubated with chondrocytes in the presence and absence of 1.5 mM CaCl2. FIG. 3B shows cell proliferation, quantified by FACS after staining cells with BrdU. Chondrocytes were incubated with 0.5, 1, and 5 mM SLFNP for 24 h before the BrdU staining. FIGS. 3C and 3D show chondrocyte protective effect of SLFNP. Chondrocytes were pre-treated with SLFNP (1 or 5 mM) or LiCl (10 mM) in the presence or absence of HA before stimulated by IL-1β (10 ng/mL). Cell viability, assessed by (3*c*) CCK-8 assay and (3*d*) live and dead assay at 48 h. Scale bars, 200 μm. FIG. 3E shows histograms showing and percentages of live cells after incubation, based on data from (3*d*). FIG. 3F shows intracellular Li+ contents. Cells were treated in the same ways as in (3*c*). The cells were lysed by acid and the lithium contents were analyzed by ICP-MS. Data are presented as mean±SD, n=3 per group. Bars with different letters are significantly different from each other (P<0.05).

Figure 4A:
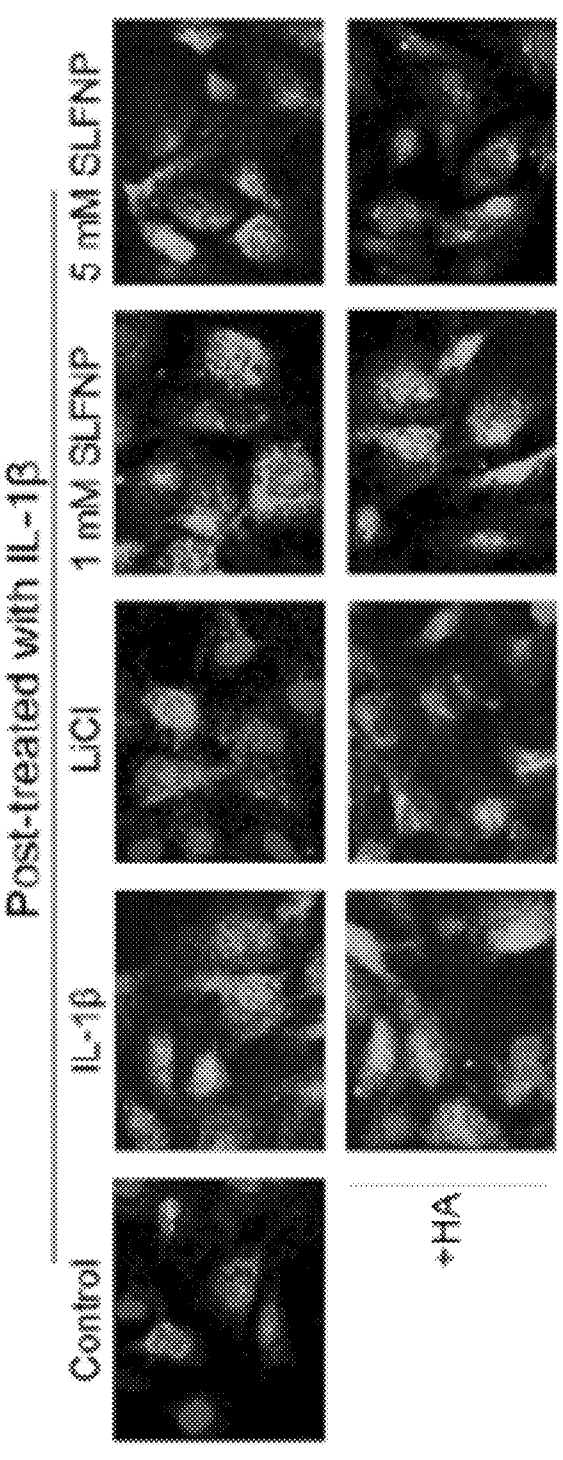

FIGS. 4A, 4B, 4C, and 4D show the effect of SLFNP to inhibit pro-inflammatory cytokine induced catabolism and to protect cartilage matrix from degradation. Chondrocytes were pre-incubated with SLFNP (1 or 5 mM) or LiCl (10 mM)±HA (50 μL) before incubation with IL-1β (10 ng/mL) for 2 days. FIG. 4A shows immunofluorescence staining to evaluate MMP-13 expression at the protein level. Scale bar, 200 μm. FIG. 4A shows qRT-PCR to assess expression of MMP13, MMP3, IL6, COX-2, ADAMTSS, iNOS, and TIMP1. FIG. 4A shows PGE2 and NO released from the chondrocytes, quantified by ELISA and Greiss reagent kit, respectively. FIG. 4A shows the impact of the treatment on cartilage matrix contents. These include expression of ACAN and COL2A1, assessed by qRT-PCR, and GAG secretion, quantified by 1, 9-dimethylmethylene blue. Data are presented as the means±SD. n=4 per group. Bars labeled with different letters are significantly different from each other (P<0.05).

FIGS. 5A and 5B show macroscopic evaluations of cartilage changes after therapy. SLFNP (1.74 μg Li) or LiCl (3.48 μg Li)±HA (50 μL 10 mg/mL) were i.a. injected once per week into Sprague-Dawley rats with surgery-induced OA. Animals were euthanized at Week 4 and 8 (n=12). FIG. 5A shows a representative photographs showing the macroscopic appearance of the cartilage from the femoral condyles. FIGS. 5B and 5C show lesion areas and depths for each treatment group at Week 4 and 8. SLFNP+HA showed the most effective cartilage protection effect, reducing the average lesion areas to 2.5 mm2 and 3.6 mm2, on Week 4 and 8, respectively, and the lesion grades to 1 and 1.5.

FIGS. 6A, 6B, and 6C show histological evaluations of cartilage changes after therapy. FIG. 6A shows H&E staining of cartilage sections after treatment for 4 and 8 weeks. Arrows: surface irregularities and fissures; asterisks: multifocal decrease in cells; triangles: increase in tissue cellularity with cloning. FIG. 6B shows safranin O staining of cartilage sections after treatment for 4 and 8 weeks. A severe reduction in aggrecan contents and overall cartilage thickness was observed after surgery. Meanwhile, treatment with SFLNP+HA was efficient in proteoglycan retention and maintaining the columnar architecture. Scale bar, 200 μm. FIG. 6C shows OARSI scores of articular cartilage after receiving treatment for 4 and 8 weeks. Values are represented as means±SD, n=12. Bars labeled with different letters are significantly different from each other (P<0.05).

FIGS. 7A, 7B, and 7C show the catabolism and serum lithium concentration changes after therapy. FIG. 7A shows a western blot to assess the expression of MMP-13, COX-2 and iNOS in cartilage after treatment for 4 and 8 weeks. FIG. 7B shows dots per inch of protein expression for MMP-13, COX-2 and iNOS, based on Western blot results from (7a). FIG. 7C shows serum lithium concentration changes. LiCl (3.48 ug Li) and SLFNP (1.74 ug Li) were i.a. injected into normal rats. Lithium contents in the blood at 0.5, 1, 4, 12, and 24 h were analyzed by ICP-MS (n=3). Values are represented as means±SD.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nanoparticle comprising a Lithium salt core is disclosed and discussed and a number of modifications that can be made to a number of molecules including the nanoparticle comprising a Lithium salt core are discussed, specifically contemplated is each and every combination and permutation of nanoparticle comprising a Lithium salt core and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

As stated above, while conventionally regarded as a non-inflammatory disease, accumulating evidence implicates inflammation in OA advancement, and there is a growing interest in exploiting anti-inflammatory treatments to reverse or slow OA progression. One promising therapeutic is lithium. Possessing a long clinical history for treatment of bipolar disorder, recent studies suggest that lithium can efficiently inhibit OA-associated catabolic events and protect the cartilage matrix from degradation. It was found that lithium reduces signaling of NF-kB and activation of p38 MAPK and STAT-3 which leads to lower expression of catabolic species that degrade cartilage. The reduction of these catabolic species in IL-1β and TNF-α induced osteoarthritis models leads to protection of chondrocytes in vitro with a significant reduction in collagenolytic activity and collagen release. In vivo, lithium was found to minimize the loss of mechanical properties in excised rat joints and decrease histologic damage scores in the knee joints of mice. Further work has suggested that lithium can inhibit Hedgehog signaling pathways by modulation of cilia on chondrocytes.

However, the administration of lithium is problematic. For bipolar disorder treatment, lithium salts are taken orally, and the serum lithium concentration is maintained below 1.5 mM to avoid systemic toxicities such as diarrhea, muscular weakness, blurred vision, coma, and even death. On the other hand, in vitro studies show that a much higher local lithium concentration is needed for effective anti-collagenolytic and anti-gelatinolytic activities (e.g. 5-10 mM). It is possible to intra articularly (i.a.) inject lithium salts to achieve high local doses, but the administration route is far from ideal as lithium is highly mobile and has a very short residence time in the joint space. For better therapeutic outcomes, an implantable drug delivery system that permits controlled release of lithium would be preferred.

In general, there have been few attempts on developing delivery systems for electrolyte-based therapeutics, in striking contrast to the contemporary research on the delivery of small molecule drugs or proteins. The underlying assumption is that electrolytes can be injected systematically, and so a new delivery strategy seems needless. However, as in the case of lithium, the local therapeutic window can exceed the serum toxicity threshold, making systematic delivery nonviable and a controlled delivery method a necessity.

Herein, a novel nanotechnology was developed for the purpose. Accordingly, in one aspect, disclosed herein are particles comprising a lithium salt core. For example, the lithium salt can be lithium fluoride (LiF) salt, lithium bromide (LiBr) salt, lithium chloride (LiCl) salt, lithium iodide (LiI) salt, lithium aluminum oxide ($LiALO_2$) salt, Lithium carbonate ($LiCO_3$) salt, Lithium phosphate ($Li_3PO_4$) salt, and/or lithium tantalum oxide ($LiTaO_3$) salt. Accordingly, disclosed herein are particles comprising a lithium salt core wherein the lithium salt is selected from the group consisting of LiF, LiCl, LiBr, LiI, $LiAlO_2$, $LiTaO_3$, $Li_3PO_4$, and $LiCO_3$.

Concentration of Li salt based on toxicity and amount needed to efficaciously reduce inflammation (i.e., the therapeutic amount). In one aspect, it is understood and herein contemplated that the therapeutically effective concentration of the lithium salt core in the particle is between about 1 and 20 mM. For example, the concentration of the lithium salt (such as, for example, LiF, LiCl, LiBr, LiI, $LiAlO_2$, $LiTaO_3$, $Li_3PO_4$, and/or $LiCO_3$) can be at least 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mM.

It is understood and herein contemplated that the size of the particle can effect the rate of elution. The size of the disclosed particle can be adjusted as needed to for the particular desired elution rate. Thus, it is understood and herein contemplated that lithium core can have a diameter between about 20 nm and about 500 nm, more preferably between about 50 nm and about 250 nm, more preferably between about 70 nm and about 200 nm, most preferably between about 90 nm and 150 nm. For example, the lithium salt core can have a diameter of about 20, 25, 30, 35, 40, 45, 50, 55, 60, 65, 70, 75, 80, 85, 90, 95, 96, 97, 98, 99, 100, 101, 102, 103, 104, 105, 106, 107, 108, 109, 110, 115, 120, 125, 130, 135, 140, 145, 150, 175, 200, 225, 250, 275, 300, 325, 350, 375, 400, 425, 450, 475, or 500 nm.

Additionally, it is understood and herein contemplated that the size of the particle can be effected by matrix used for synthesis. In one aspect, the synthesis matrix can comprise silicone, polyvinyl alcohol (PVA), sodium polyacrylate, polyethylene oxide, polyethylene glycol (PEG), ethylene glycol (EG), polyvinylpyrrolidone, use polyvinylpyrrolidone (PVP), poly(acrylic acid) (PAA), polyethylenimine (PEI), poly-methyl methacrylate, and any co-polymer, ter-polymers, or combination thereof. For example, the core can be synthesized in a synthesis matrix comprising a polyethylene glycol:ethylene glycol mixture. It is understood and herein contemplated that where a mixture of hydrogel synthesis matrix materials is used, the ratio of the mixture can effect the rate of elution of the lithium salt as well as the size of the particle which consequently effects the rate of elution of the lithium salt in an eluting matrix (such as, for example a hydrogel). For example, in one aspect, disclosed herein are hydrogel synthesis matrixes comprising a mixture of polyethylene glycol and ethylene glycol, as the ratio of PEG to EG increases the particle size In one aspect, disclosed herein are particles, wherein the synthesis matrix comprises a 0.5:1, 0.6:1, 0.7:1, 0.8:1, 0.9:1, 1:1, 1.1:1, 1.2:1, 1.3:1 1.4:1, 1.5:1, 1.6:1, 1.7:1, 1.8:1, 1.9:1, 2:1, 2.5:1, 3:1, 4:1, or 5:1 ratio of polyethylene glycol:ethylene glycol.

Although the Li salt nanoparticle will deliver and slowly release the Li salt into the site of administration, the Li salt matrix is still susceptible to exposure to the microenvironment and could be rapidly hydrolyzed thus, minimizing efficacy. Accordingly, it was contemplated that the lithium salt particle should be encapsulated in a shell that would minimize hydrolysis and thus form a particle with a core and shell. The core comprising the lithium salt and eluting matrix and the shell the protective outer layer. Thus, in one aspect, disclosed herein are particles comprising a lithium core (such as, for example, a lithium core comprising a therapeutically effective concentration of a lithium salt) and an encapsulating shell.

Briefly, a silica coated lithium fluoride nanoparticle, or SLFNP (both singular and plural), was synthesized, which consists of a ~100 nm LiF core and a ~20 nm silica shell. The silica coating blocks the LiF core from direct exposure to the bulk water, preventing its rapid hydrolysis. Meanwhile, the coating does allow for slow permeation of water molecules, which will slowly degrade the LiF particle, causing sustained release of lithium to the surroundings. Accordingly, in one aspect, disclosed herein are particles comprising a lithium core (such as, for example, a lithium core comprising a therapeutically effective concentration of a lithium salt) and an encapsulating shell, wherein the encapsulating shell can comprise a silica outer layer such as a tetraethyl orthosilicate outer layer. In one aspect, it is contemplated herein that the thickness of the shell can effect the rate of hydrolosis of the lithium salt core. Thus, in one aspect, the thickness of the encapsulating shell is at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 nm.

It is understood and herein contemplated that a lithium salt, if administered alone, would elute out systemically and not be retained at the sight of inflammation thereby increasing systemic toxicities and reducing efficacy. In one aspect, the lithium can comprise a hydrogel eluting matrix material comprising hyaluronic acid, alginate, collagen, chondroitin sulfate, chitosan, and xanthan gum, and their cross-linked derivatives. It is understood and herein contemplated that for each of the eluting matrix materials is used, the concentration of the hydrogel and/or ratio of the mixture can effect the rate of elution of the lithium salt.

In one aspect, the particles can be combined with existing clinical treatment options, including COX-2 inhibitors, non-steroidal anti-inflammatory drugs (NSAIDS), hyaluronic acid (HA), and steroids which can reduce symptoms of inflammation while the lithium particles treat the underlying condition or disease. For example, silica coated lithium salt nanoparticles (such as, for example silica coated lithium fluoride nanoparticles (SLFNP)) can be loaded into HA, which is widely used in the clinic for OA management, and administered into the joint space of a patient. Unlike highly mobile lithium salts, the nanocrystal structure prevents fast diffusion of lithium; instead, the LiF core is slowly degraded in the aqueous surroundings and it acts as a source for controlled release of the anti-inflammatory lithium ion (FIG. 1*a*). Meanwhile, fluoride is efficiently sequestered by the incoming calcium to form non-toxic calcium fluoride. Such a sustained release of lithium, in conjunction with the viscosupplementory effects of HA, elicits effective chondrocyte protection, while inducing no local and systematic toxicities. This was verified first in vitro with normal rat articular chondrocytes, and then in vivo with surgically induced rat OA models. Thus, in one aspect, disclosed herein are particles comprising a lithium core (such as, for example, a lithium core comprising a therapeutically effective concentration of a lithium salt) and an encapsulating shell wherein the particle is loaded into HA (for example a SLFNP+HA composition). In some aspects, the HA can further comprise Calcium to sequester the fluoride from the LiF salt.

In one aspect, the disclosed particles can comprise a pharmaceutical composition alone or in combination with traditional treatment options, including COX-2 inhibitors, nonsteroidal anti-inflammatory drugs (NSAIDS), hyaluronic acid (HA), and steroids. Thus, in one aspect, disclosed herein are pharmaceutical compositions comprising a lithium core (such as, for example, a lithium core comprising a therapeutically effective concentration of a lithium salt) and an encapsulating shell (such as, for example, SLFNP). Also disclosed herein are pharmaceutical compositions comprising a lithium core (such as, for example, a lithium core comprising a therapeutically effective concentration of a lithium salt) and an encapsulating shell (such as, for example, SLFNP) further comprising HA.

1. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2: 447-451, (1991); Bagshawe, K. D., *Br. J. Cancer,* 60: 275-281, (1989); Bagshawe, et al., *Br. J. Cancer,* 58: 700-703, (1988); Senter, et al., *Bioconjugate Chem.,* 4: 3-9, (1993); Banelli, et al., *Cancer Immunol. Immunother.,* 35: 421-425, (1992); Pietersz and McKenzie, *Immunolog. Reviews,* 129: 57-80, (1992); and Roffler, et al., *Biochem. Pharmacol,* 42: 2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49: 6214-6220, (1989); and Litzinger and Huang, *Biochimica et Biophysica Acta,* 1104: 179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including lithium salt particles, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous injection or drip, subcutaneous, intraperitoneal, intraarticular or intramuscular injection. The disclosed nanoparticles can be administered intravenously, intraperitoneally, intramuscularly, intra articularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

For bipolar disorder treatment, lithium salts are taken orally, and the serum lithium concentration is maintained below 1.5 mM to avoid systemic toxicities such as diarrhea, muscular weakness, blurred vision, coma, and even death. On the other hand, in vitro studies show that a much higher local lithium concentration is needed for effective anti-collagenolytic and anti-gelatinolytic activities (e.g. 5-10 mM). It is possible to intra articularly (i.a.) inject lithium salts to achieve high local doses, but the administration route is far from ideal as lithium is highly mobile and has a very short residence time in the joint space. For better therapeutic outcomes, an implantable drug delivery system that permits controlled release of lithium would be preferred.

It is understood that the pharmaceutical compositions of any preceding aspect can be used to treat a subject with an inflammatory condition, such as, for example, osteoarthritis, rheumatoid arthritis, ankylosing spondylitis, and psoriasis. Accordingly, in one aspect, disclosed herein are methods of treating an inflammatory disease or condition (such as, for example, osteoarthritis) comprising administering to the subject particles comprising a lithium core (such as, for example, a lithium core comprising a therapeutically effective concentration of a lithium salt) and an encapsulating shell (such as, for example, a silica shell). In one aspect the particles administered to the subject can be loaded into loaded into HA and/or combined with some other traditional form of treatment for inflammation, including, but not limited to COX-2 inhibitors, nonsteroidal anti-inflammatory drugs (NSAIDS), and/or steroids.

As noted above, the particles can be administered via any route suitable for treatment of an inflammatory condition including, but not limited to intravenous, intraperitoneal, intramuscular, intra articular, subcutaneous, intracavity, transdermal, and topical administration.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Results

(1) Synthesis and Characterization of LiF Nanoparticles

LiF nanoparticles were synthesized through a co-precipitation method. LiF was selected because of its moderate water solubility (0.13 g/100 mL at 25° C.). As a comparison, other common lithium salts have either too high a solubility (e.g. 84.5 and 170 g/100 mL, for LiCl and LiBr, respectively), or are virtually insoluble (e.g. $LiAlO_2$ and $LiTaO_3$). For the synthesis, lithium nitrate was dissolved in a mixed solvent of ethylene glycol (EG)/poly(ethylene glycol) (PEG, MW=300). Into the mixture, ammonium fluoride in EG was dropwise added, followed by gentle magnetic stirring at room temperature. In a typical synthesis, a 1:1 PEG/EG ratio was used, and ~100 nm cubic LiF nanoparticles yielded (FIGS. 1*b* and 1*c*). Increasing the PEG/EG ratio produced particles of smaller sizes (FIG. 2), likely due to the stronger surface interaction with PEG than with EG. X-ray powder diffraction (XRD) confirmed that the resulting nanoparticles were mainly cubic LiF (Fm-3m, JSPDF No.: 45-1460, FIG. 1*d*). FT-IR observed a broad peak centered at 3386 cm-1, which is attributed to the —OH absorption from the PEG coating.

(2) LiF Nanoparticle Degradation and Fluoride Sequestration

The as-synthesized LiF nanoparticles degraded rapidly in water. To retard the process, LiF nanoparticles were coated with a layer of silica using a Stober method (FIGS. 1*e* and 1*f*). Lithium release was analyzed in PBS by inductively coupled plasma mass spectrometry (ICP-MS). Uncoated LiF particles had completely liberated their lithium content within 1 hour of water exposure (FIG. 1*f*). For silica coated LiF nanoparticles (i.e. SLFNP), the particle lifetimes were markedly increased (FIG. 10. Specifically, the degradation time was ~24 h for 5 nm coating, ~65 h for 20 nm coating, and even longer when 50 nm coating was used. Considering that it takes ~60 h for i. a. injected HA to fully degrade in the joint, the 20-nm-coating formulation was chosen for further studies.

The lithium release was also investigated when SLFNP were loaded into HA or in the presence of 1.5 mM Ca2+ (which is the extracellular calcium concentration). Under both conditions, neither acceleration nor deceleration of lithium release (FIG. 1*f*) was observed. However, in the latter case, energy dispersive spectroscopy (EDS) found a gradually increased calcium content in the particles while the fluoride content remained almost unchanged. This indicates that unlike lithium, fluoride was not liberated to the surroundings, but was sequestered by the incoming calcium to form stable calcium fluoride.

(3) Impact of SLFNP on Chondrocyte Viability

Using a CCK-8 assay, the cytotoxicity of SLFNP was evaluated on articular chondrocytes isolated from normal rat knee joints. In normal culture medium, no toxicity was observed when the particle concentration was below 5 mM (lithium concentration, the same below unless specified otherwise; FIG. 3*a*). When the incubation medium was supplemented with 1.5 mM Ca2+, SLFNP showed no toxicity through 20 mM (FIG. 3*a*, blue curve). The improved tolerance in the latter case was owing to effective F-sequestration by calcium, which is a good mimic of the reality. For safety purposes, however, a maximum of 5 mM of SLFNP was used in further in vitro studies. The impact of SLFNP was also investigated on cell proliferation by labeling cells with bromodeoxyuridine (BrdU). For 5 mM SLFNP, flow cytometry found a comparable level of positive BrdU staining relative to the PBS control (30.64% vs. 33.98%), again indicating minimal toxicity (FIG. 3*b*).

The capacity of SLFNP was assessed to protect chondrocytes from deterioration induced by inflammatory cytokines. Chondrocytes were first incubated with SLFNP and then added to the medium 10 ng/mL interleukin-1-beta (IL-1β), a major inflammatory cytokine involved in chronic OA. For comparison, chondrocytes were treated with PBS or LiCl salt (10 mM) before adding IL-1β. In the PBS group, CCK-8 assay found a marked drop of cell viability (37.64% at 48 h). Both SLFNP and LiCl mitigated the toxicity, increasing viability to 54.75% and 67.40% for 1 and 5 mM SLFNP, and 80.77% for LiCl, respectively (FIG. 3*c*). The observation was validated by live/dead assays, which found extensive positive ethidium homodimer-1 staining in the PBS group, and a significantly reduced level of positive staining when chondrocytes were treated with SLFNP or LiCl (FIGS. 3*d* and 3*e*).

The chondroprotective effect was also assessed when SLFNP or LiCl were loaded into HA. Compared to SLFNP alone, SLFNP+HA led to improved viability (82.76% for 5 mM SLFNP+HA, P<0.01). Conversely, worse protective effect was observed with LiCl+HA than with LiCl alone (64.25%, P<0.05, FIG. 3*e*). The cause of the differed effect is unknown, but is presumably due to the impact of HA on lithium uptake. For LiCl, the main form of lithium is Li+; it is poorly retained in HA and its entry into cells can be blocked by the gel. For SLFNP+HA, on the other hand, lithium can enter cells as either an ion or a nanoparticle; in the latter case, the cell uptake can be facilitated by HA mediated endocytosis. To confirm, intracellular lithium contents were analyzed by ICP-MS. Compared to SLFNP alone, SLFNP+HA exhibited an increased lithium uptake (1.71 vs. 1.18 pg/cell, P<0.05); whereas LiCl+HA caused a decreased lithium content compared to LiCl alone (0.98 vs. 1.53 pg/cell, P<0.05. FIG. 3*f*).

For both SLFNP and LiCl salt, lithium remained in the incubation medium throughout the in vitro study. This differs from the reality in which lithium diffuses continuously out of the joint space after injection, described further below. Hence, the benefits of controlled lithium release with SLFNP did not fully manifest in the cellular experiments.

(4) Anti-Inflammation Effects of SLFNP

The impact of SLFNP was assessed on key catabolic biomarkers involved in OA. These include MMP13, an important collagenase involved in OA progression. Immunofluorescence staining found a marked increase of MMP13 expression in chondrocytes after IL-1β stimulation (10 ng/mL, FIG. 4*a*); the upregulation was attenuated when cells were pre-incubated with SLFNP or LiCl. This is concomitant with qRT-PCR analysis, finding that the MMP13 mRNA level was increased by 15.4-fold after IL-1β induction, and reduced by 32.16% when cells were pre-incubated with SLFNP (5 mM).

MMP13 expression was also evaluated when treating chondrocytes with HA, SLFNP+HA, and LiCl+HA. While HA alone showed little inhibitive effect (relative mRNA level of 14.65, P=0.18), its combination use with SLFNP led to a significantly reduced MMP13 expression (relative mRNA level of 6.73, P<0.01). Conversely, cells treated with LiCl+HA exhibited an even higher level of MMP13 than LiCl (9.023, P<0.05). This is attributed to the differing impact of HA on lithium uptake, which was observed in vitro (FIG. 3*e*).

Figure 4B:
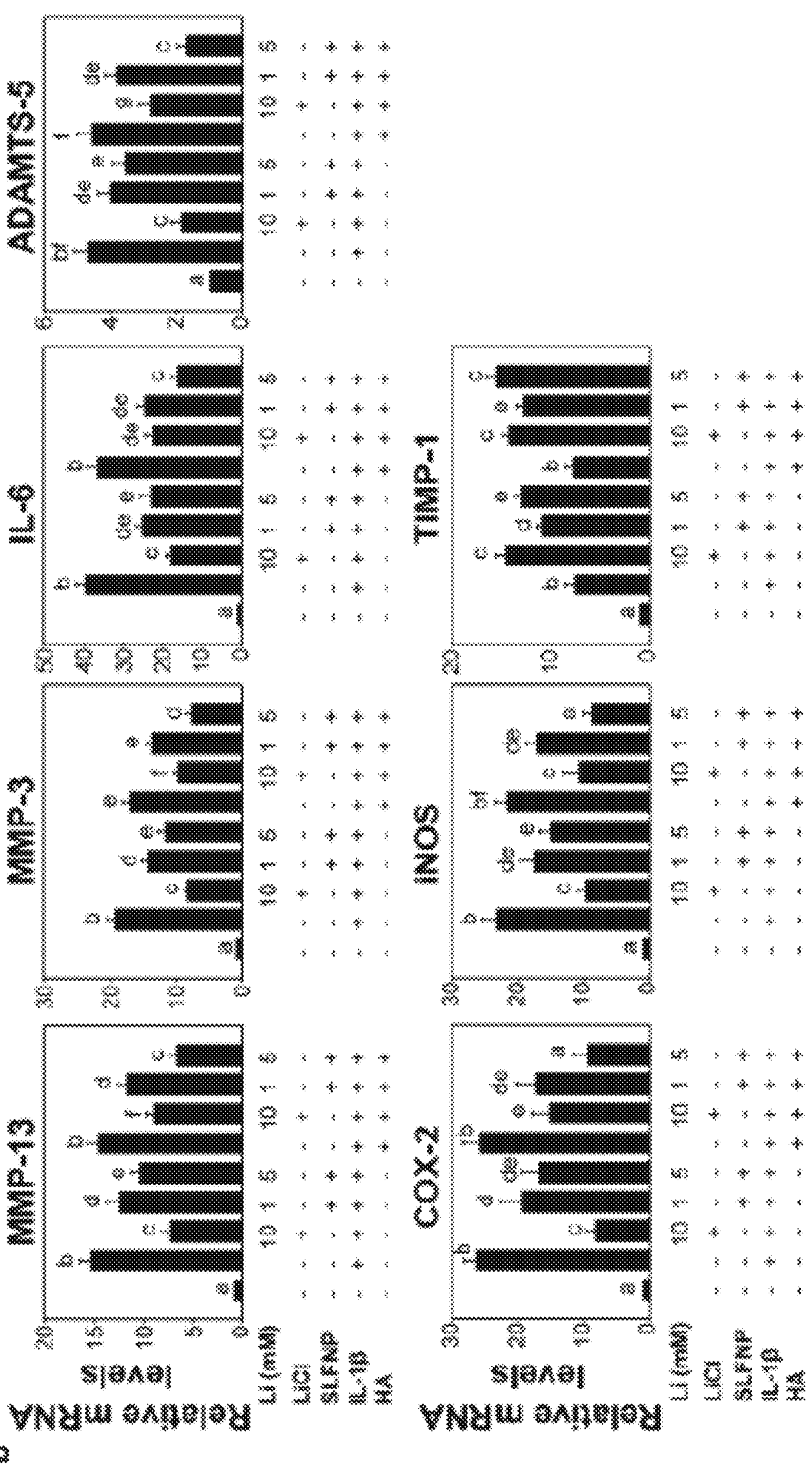

Other OA-related catabolic markers were also assessed, including MMP3, IL6, COX-2, ADAMTSS, and iNOS. For all of the biomarkers, SLFNP+HA showed the most pronounced anti-catabolism effect. Specifically, compared to IL-1β-stimulated cells, SLFNP+HA treatment reduced the mRNA levels of MMP3, IL6, ADAMTSS, COX-2, and iNOS by 60.63%, 41.20%, 64.15%, 64.38% and 62.18% (FIG. 4*b*). These are overall superior to either LiCl (57.45%, 54.94%, 59.77%, 68.29%, and 57.66%) or LiCl+HA (49.14%, 42.76%, 40.00%, 41.62%, and 53.44%). For ADAMTSS and iNOS, their enzymatic products were also quantified PGE2 and NO. In accordance with the qRT-PCR results, there was a drastic increase of PGE2 and NO production upon IL-1β stimulation (to 4.92±0.26 μM and 10006±591 pg/mL, respectively), and the up-regulation was markedly attenuated when cells were treated with SLFNP (3.02±0.12 μM and 7466±303 pg/mL), and further suppressed when HA was added (1.96±0.18 μM and 7020±478 pg/mL, FIG. 4*c*). On the contrary, the expression of TIMP1, a natural inhibitor of MMPs, was increased with SLFNP (13.0 fold increase in mRNA level relative to the IL-1β stimulation control) and the up-regulation was further enhanced with SLFNP+HA (15.5 fold increase).

The suppressed catabolism led to a reduction in cytokine-induced loss of main cartilage matrix contents, including type II collagen, aggrecan, glycosaminoglycan (GAG). Compared to normal chondrocytes, incubation with IL-1β

Figures 4C, 4D:
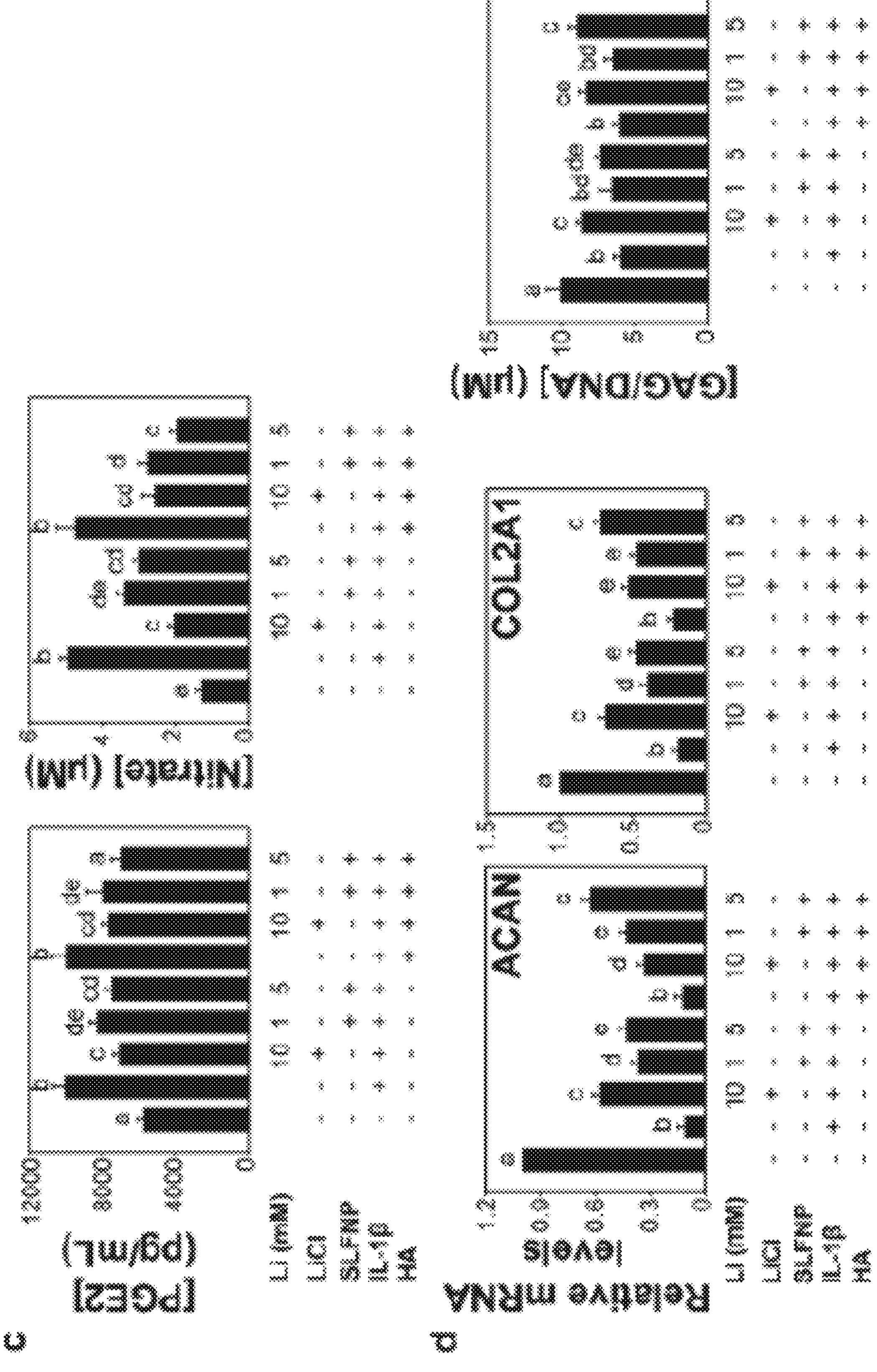

(10 ng/mL) reduced the relative mRNA levels of ACAN and COL2A1 by 89.1% and 81.5%, respectively, and the secretion of GAG (measured in GAG/DNA) from 10.09±0.81 to 5.92±0.51 mg/mL (FIG. 4*d*). The collagen loss was also validated by immunohistochemical staining with 1,9-dimethylmethylene blue. SLFNP+HA (5 mM) elevated the mRNA levels of ACAN and COL2A1 compared to IL-1β reduction by 5.73 fold and 3.86 fold, respectively, and the GAG level to 8.96±0.49 mg/mL.

(5) In Vivo Study With Rat OA Models

In vivo analysis was performed in Sprague-Dawley rats which had undergone bilateral anterior cruciate ligament transection (ACTL) surgery. One month after the surgery, the animals were randomly sorted into six groups (n=24) and were i.a. injected once per week with the following regimens: SLFNP+HA (1.74 μg Li in 50 μL HA), SLFNP alone (1.74 μg Li in 50 μL PBS), LiCl+HA (3.48 μg Li in 50 μL HA), LiCl alone (3.48 μg in 50 μL PBS), HA alone (50 μL), and PBS (50 μL). For control, a sham-operated group was also studied.

For all groups, no animal death was observed nor reduced daily activity throughout the study. Selected animals were sacrificed in each group at Week 4 and Week 8 (n=12 at each time point), and removed the condyles and plateaus from the joints. For the sham-operated group, the cartilage manifested a smooth and glistening surface, showing no detectable lesions. In the PBS-treated ACTL group, on the other hand, characteristic OA features were identified such as erosion, osteophyte formation, and large areas of lesions (FIG. 5*a*). It was also found that the lesion area was increased between Week 4 and Week 8 (10.0 and 12.8 mm2, respectively; lesion depth grade 3), indicating continuous OA progression. Treatment with SLFNP led to moderate OA regression, showing average lesion areas of 7.1 mm2 and 8.8 mm2 at Week 4 and 8; these were slightly better than LiCl alone (8.5 mm2 and 10.2 mm2 on Week 4 and 8; P<0.05, FIGS. 5*b* and 5*c*).

Unlike the in vitro studies, HA showed better cartilage protection than both SLFNP and LiCl, reducing the average lesion area to 5.4 mm2 and 7.4 mm2 at Week 4 and 8, and lowering the lesion depth grade to 2. This is because HA the viscosupplementation effect of HA and an improved shock absorbing ability it induced, benefits that do not manifest in vitro. Compared to HA, the combination use of LiCl and HA led to further a reduced lesion size (6.5 mm2 on Week 8) but the improvement was insignificant (P=0.15). As discussed above, this is because HA does not improve Li+ retention in the joint space and can even adversely affect the uptake of the ion by chondrocytes. Conversely, SLFNP+HA showed much greater cartilage protection effect than either HA or SLFNP alone. The combination reduced the average lesion areas to 2.5 mm2 and 3.6 mm2, at Week 4 and 8. These account for a remarkable reduction of 77.0% and 71.8% relative to the PBS control. Concomitantly, the lesion grades were reduced to 1 and 1.5 at Week 4 and 8 (FIGS. 5*b* and 5*c*).

The cartilage changes were further assessed histologically by hematoxylin-eosin (H&E) staining and Safranin O-fast green staining. Compared to the sham control, H&E staining found extensive morphological and cellular changes in the surgery (PBS) group. These include surface irregularities and fissures (FIG. 6*a*, black arrows), multifocal decrease in cells (FIG. 6*a*, asterisks), increase in tissue cellularity with cloning (FIG. 6*a*, black triangles), along with full-depth erosion and widespread cell loss. Meanwhile, Safranin O-fast green staining identified a reduced level of aggrecan contents and overall cartilage thickness, indicating severe cartilage matrix degradation (FIG. 6*b*). Treatment groups exhibited varied degrees of improvement with regard to morphological changes, proteoglycan retention, and tidemark integrity promotion. Among them, SFLNP+HA was the most effective in maintaining the columnar architecture of normal cartilage. Based on the histological results, OARSI scores were assigned to each sample (FIG. 6*c*). Compared to the PBS control, the SLFNP+HA regimen reduced the OARSI score by 79.29% and 71.07% at Week 4 and 8, respectively. As a comparison, the reduction amplitudes were 19.28% and 11.95% for LiCl, and 54.29% and 44.03% for HA.

Finally, immunoblotting was used to analyze the impact of the treatments on catabolic markers including MMP13, COX-2 and iNOS (FIG. 7*a*). Compared to the PBS control, all the lithium and HA regimens led to down-regulation of the three biomarkers. In agreement with the macroscopic and histological analyses, SLFNP+HA elicited the most effective inhibition, reducing MMP13, COX-2 and iNOS in the cartilage by 73.67%, 63.89%, and 74.08%, respectively, at Week 4, and 51.48%, 58.58%, and 59.91% at Week 8 (FIG. 7*b*).

(6) Serum Lithium Concentration Analysis

Last but critically, the serum lithium content was analyzed after i.a. injection of LiCl or SLFNP+HA (FIG. 7*c*). For LiCl, the serum lithium concentration spiked early then, continuously decreased after injection and was reduced to a background level between 4 and 24 h. This was attributed to the fast clearance of Li+ from the joint space. For SLFNP+HA, on the other hand, the serum concentration was maintained between at 0.013-0.018 mM for more than 24 h, which was attributed to the particle's controlled lithium release. Such a serum concentration is several orders of magnitudes lower than the 1.5 mM toxicity threshold. Indeed, while inducing efficient local OA control, the SLFNP+HA treatment caused no detectable systematic toxicity, which was confirmed by H&E staining with organs such as the liver, kidney, spleen, heart, lung, and brain.

b) Conclusions

In summary, a novel implantable drug delivery system for lithium-based therapeutics was developed. While there has been extensive research on the controlled release of small molecule drugs and proteins, few attempts have made with electrolyte-based therapeutics. By utilizing a LiF nanocrystal, silica coating of appropriate thickness, and HA as a delivery medium, controlled release of lithium within OA-bearing joints was successfully achieved. This improves bioavailability of the anti-inflammatory agent, leading to remarkable down-regulation of catabolic OA mediators and effective protection of cartilage. There is an unmet need for non-surgical treatment options to alter the course of OA disease progression. The current study provides a novel, effective, and low-toxic OA therapy that holds great potential in clinical translation for this disease and more.

c) Methods (1) Synthesis of Lithium Fluoride Nanoparticles

In a typical synthesis, 0.5 mL of 0.25 M lithium nitrate in ethylene glycol (EG) was mixed with 2 mL of EG and 3 mL of poly(ethylene glycol) (MW 300, PEG-300). After stirring for 10 min, 1.0 mL of 0.375 M ammonium fluoride in ethylene glycol was added dropwise and the vial was stirred at room temperature for 1 h. The as-synthesized NPs were purified by centrifugation at 9682 rcf for 10 min and washed 3 times with ethanol. The size of LiF NPs can be adjusted by changing the ratio between EG/PEG, with smaller particles synthesized with a higher PEG content.

(2) Characterization of LiF Nanoparticles

Transmission electron microscope (TEM) images were acquired on a FEI Tecnai 20 operated at 200 kV. High resolution TEM, selected area electron diffraction, and energy dispersive X-ray spectra (EDS) was characterized carried out on a Hitachi transmission electron microscope H9500 operating at 300 kV accelerating voltage. Scanning electron microscope (SEM) images and elemental mapping were also taken on a FEI Teneo operating at 5 kV for images and 10 kV for elemental mapping. STEM data was collected on a Hitachi HD 2000 operating at 200 kV. X-ray diffraction (XRD) analysis was carried out on a Bruker D8-Advance using dried sample on a cut glass slide with Cu K$\alpha$1 radiation ($\lambda$=1.5406 Å). Fourier-transform infrared (FT-IR) spectra were recorded on a Nicolet iS10 FT-IR spectrometer.

(3) Synthesis of Silica Coated LiF Nanoparticles

LiF nanoparticles were mixed with 5 mL of ethanol and 0.2 mL of ammonia (28%) for 30 min. Tetraethyl orthosilicate (5 to 30 μL, depending on the coating thickness) was dropwise added, and the resulting solution was stirred overnight. The process produces a silica coating of variable thickness (5-50 nm). To load SLFNP into HA, 0.4 mL SLFNP aqueous solution (500 mM) was added dropwise into 1 mL of HA (10 mg/mL, Shanghai Jingfeng, Shanghai, China) and agitated the solution for 15 min. For the LiCl+HA control, LiCl of the same lithium concentration was dropwise added to HA.

(4) Lithium Release

As-synthesized LiF nanoparticles, SLFNP of different coating thickness, or SLFNP in HA (20 nm coating, 3 mg of SFLNP in 2 mL of 1 wt % HA solution), were loaded onto a Slide-A-Lyzer dialysis cassette and dialyzed against 20 mL of PBS. For comparison, the lithium release of SLFNP+HA in PBS in the presence of 1.5 mM of Ca2+ was studied. At selected time points, 0.1 mL of the external solution was removed and the lithium concentration was determined by inductively coupled plasma mass spectrometry (ICP-MS). 0.1 mL of fresh PBS (or PBS+Ca2+) was added to the dialysis system.

(5) Articular Chondrocytes Culture

The articular chondrocytes were isolated from the knee joints of 1-week-old Sprague-Dawley (SD) rat using enzymatic digestion. To remove other tissues and cells, the cartilage from the knee joints was trysonized with 0.25% (v/v) trypsin (Solarbio, China) for 30 min under sterile conditions and then released with 2 mg/mL collagenase type II (Gibco, USA) for 3 h. After centrifugation, the chondrocytes were cultured in alpha-modified Eagle's medium ($\alpha$-MEM, Gibco, USA) containing 10% (v/v) fetal bovine serum (FBS, Gibco, USA) and 1% (v/v) penicillin/streptomycin (Solarbio, China). The cells were then incubated to a humidified incubator with 5% CO2 at 37° C. and the culture medium was replaced every other day. Articular chondrocytes at passage 2 were trypsinized and collected for further studies.

(6) Cytotoxicity of SLFNP on Chondrocytes

The cytotoxicity was evaluated using a cell counting kit-8 (CCK-8, Sigma, USA) assay. The articular chondrocyte cells were incubated in 96-well plates with SLFNP at varying concentrations of lithium (0.5-20 mM). For higher concentrations (8-20 mM), 1.5 mM of CaCl2 was added to the incubate medium. After 48 h incubation, CCK-8 reagent was added to the culture medium and the chondrocytes were furtherer incubated at 37° C. for 4 h. 450 nm absorbance was measured on a microplate reader (Thermo Fisher Scientific, USA). All measurements were performed sextuplicate.

(7) Flow Cytometry

A cell proliferation detection kit (BD Biosciences, USA) based on 5-bromo-2-deoxyuridine (BrdU, BD Biosciences, USA) was used to study the proliferative response of chondrocytes after treatments with SLFNP. After 2 days of SLFNP treatment, the chondrocytes were incubated with BrdU for 2 h. The cells were then stained with FITC-conjugated BrdU antibodies and analyzed by flow cytometry. Actively proliferating cells were quantified as the ratio of BrdU-positive cells to the total cells.

(8) IL-1β Induced Chondrocytes and Chondroprotective Effect

Cells were divided into nine groups: (1) Control: chondrocytes treated with SLFNP; (2) IL-1β: chondrocytes treated with 10 ng/mL IL-1β (Gibco, USA) and cultured for 2 days; (3) LiCl+IL-1β: chondrocytes pre-incubated with LiCl for 1 h followed by treatment with 10 ng/mL IL-1β for 2 days; (4) 1 mM SLFNP+IL-1β: chondrocytes pre-incubated with 1 mM SLFNP for 1 h followed by treatment with IL-1β for 2 days; (5) 5 mM SLFNP+IL-1β: chondrocytes pre-incubated with 5 mM SLFNP for 1 h followed by treatment with IL-1β for 2 days; (6) HA+IL-1β: condrocytes pre-incubated with 10 mg/mL HA for 1 h followed by treatment with IL-1β for 2 days; (7) HA+LiCl+IL-1β: chondrocytes pre-incubated with 10 mM LiCl and HA for 1 h followed by treatment with IL-1β for 2 days; (8) HA+1 mM SLFNP+IL-1β: chondrocytes pre-incubated with 1 mM SLFNP and HA for 1 h followed by treatment with IL-1β for 2 days; (9) HA+5 mM SLFNP+IL-1β: chondrocytes pre-incubated with 5 mM SLFNP and HA for 1 h followed by treatment with IL-1β for 2 days.

(9) Live/Dead Assay

Cells were treated as the same procedures as described above. Live/dead assays were performed using a live/dead viability assay kit (Invitrogen, USA) after 2 days of culture. Briefly, cells were incubated in a solution containing 0.5 mM of calcein AM and 0.5 mM of ethidium homodimer-1 for 40 min at room temperature in the dark. Then the plates were washed with PBS before observed under a fluorescent microscope (OLYMPUS, Japan).

(10) Lithium Levels in Cells

Chondrocytes pre-treated with SLFNP or LiCl for 1 h were stimulated with IL-1β for 2 days, washed thoroughly with PBS, then trypsinized and collected. Using aliquots of 100 μL cell suspensions taken from each sample, the number of cells was determined, with the remainder sonicated for 3-5 min. The cells were then lysed by nitric acid and the lithium levels in cells were determined using ICP-MS (Thermo Fishier, USA).

(11) Histological Examination In Vitro

For in vitro studies, cells in all groups were fixed in 4% (v/v) paraformaldehyde after washing in PBS for three times. After fixation, the cells were stained with safranin O (Sigma, USA) for histological evaluation of the GAG degradation. Images were acquired on a light microscope (OLYMPUS, Japan).

(12) Quantitative Real-Time Polymerase Chain Reaction (qRT-PCR)

RNA was isolated from chondrocytes in all groups after 2 days of treatment using an RNA isolation kit (Tiangen Biotechnology). The primer sequences and number used are presented in Table 1.

TABLE 1

Primer sequences used in qRT-PCR experiments.

| mRNA | Forward Primer | Reverse Primer |
|---|---|---|
| IL6 | 5'-CACTTCACAAG TCGGAGGCT-3' (SEQ ID NO: 1) | 5'-TCTGACAGTGC ATCATCGCT-3' (SEQ ID NO: 2) |
| ADAMTS5 | 5'-CCCAAATACGC AGGTGTCCT-3' (SEQ ID NO: 3) | 5'-ACACACGGAGT TGCTGTAGG-3' (SEQ ID NO: 4) |
| COX2 | 5'-GATGACGAGCG ACTGTTCCA-3' (SEQ ID NO: 5) | 5'-CAATGTTGAAG GTGTCCGGC-3' (SEQ ID NO: 6) |
| iNOS | 5'-GCTTGGGTCTT GTTAGCCTAGT-3' (SEQ ID NO: 7) | 5'-ATTCTGTGCAG TCCCAGTGAG-3' (SEQ ID NO: 8) |
| MMP3 | 5'-GGCTGTGTGC TCATCCTACC-3' (SEQ ID NO: 9) | 5'-TGGAAAGGTAC TGAAGCCACC-3' (SEQ ID NO: 10) |
| MMP13 | 5'-GGATCCATGA TGGCACTGCT-3' (SEQ ID NO: 11) | 5'-TGGCTTTTGCC AGTGTAGGT-3' (SEQ ID NO: 12) |
| TIMPI | 5'-GCTTTCTGCAA CTCGGACCT-3' (SEQ ID NO: 13) | 5'-TCTCCATGGCT GGGGTGTAG-3' (SEQ ID NO: 14) |
| ACAN | 5'-CCGCTGGTCTG ATGGACACT-3' (SEQ ID NO: 15) | 5'-AGGTGTTGGGG TCTGTGCAA-3' (SEQ ID NO: 16) |
| COL2A1 | 5'-CTGGTCCTTCC GGCCCTAGA-3' (SEQ ID NO: 17) | 5'-GGATCGGGGCC CTTCTCTCT-3' (SEQ ID NO: 18) |
| β-actin | 5'-CCCATCTATGA GGGTTACGC-3' (SEQ ID NO: 19) | 5'-TTTAATGTCAC GCACGATTTC-3' (SEQ ID NO: 20) |

Using a reverse transcription kit, cDNA was synthesized from 300 ng total RNA (Fermentas, USA). qRT-PCR reactions were then carried out using a Quantitative PCR Detection System (Realplex 4, Eppendorf Corporation) with FastStart Universal SYBR Green Master (Mix, Roche, Swit) at conditions of 10 min at 95° C., 15 s at 95° C. and 1 min at 60° C., and simultaneously collected data of melting curves for PCR specificity verification. To calculate qRT-PCR validation, the 2-ΔΔCT method was employed with gene expressions normalized based on the cycle threshold (CT) values for each gene and β-actin.

(13) Immunofluorescence

After 2 days of culture, cells in the different treatment groups were washed twice with PBS, fixed in 4% formalin for 20 min, and permeabilized with 0.3% Triton X-100 (WN) in PBS for 10 min. After blocking with 5% BSA in PBS for 1 hour at room temperature, primary MMP-13 antibodies were added (1:200 dilution, Abcam, USA) and incubated at 4° C. overnight. After incubation with fluorescent secondary antibodies (Licor, USA) at room temperature for 1 h, samples were examined under a fluorescent microscope (OLYMPUS, Japan).

(14) Nitric Oxide (NO) and Prostaglandin E2 (PGE2) Release

To assess the production of NO from IL-1(3-induced chondrocytes pretreated with SLFNP or LiCl, the amount of extracellular nitrite was measured using a Greiss reagent kit (Invitrogen, USA). Briefly, 150 μL of culture supernatant was incubated with 20 μL of Greiss reagent and 130 μL of deionized water. After 30 min of incubation at room temperature, absorbance at 548 nm was measured using a plate reader (Thermo Fishier, USA). A photometric reference sample was prepared by mixing 20 μL of Griess Reagent and 280 μL of deionized water. PGE2 was quantified using enzyme-linked immunosorbent assay (ELISA, R&D Systems, USA) by following the vendor provided protocol. The absorbance at 450 nm was measured using a plate reader (Thermo Fishier, USA).

(15) DNA and GAG Contents

Chondrocytes were harvested and digested after treatments with 1 mL of proteinase K solution (Invitrogen, USA) and incubated overnight at 60° C. Homogenized samples were fluorocrome-tagged with Hoechst 33258 dye (Sigma, USA) and analyzed the DNA content of the chondrocytes with a plate reader (Thermo Fishier, USA) (excitation/emission: 360 nm/460 nm). Double stranded DNA from calf thymus (Sigma, USA) was the standard used to calculate the mass of DNA present in each sample.

For GAG content, 1,9-dimethylmethylene blue (DMMB, Sigma, USA) dye was used on the homogenized samples in the DNA assay. Color reagent and cell lysate were combined and the mixture was incubated for 5 min. The absorbance at 525 nm was measured by a plate reader (Thermo Fisher, USA) and compared to a standard curve established with chondroitin sulfate (Sigma, USA). GAG content was then normalized to the total DNA content for each sample.

(16) In Vivo OA Induction and Treatment

Sprague Dawley Rats (SD rats) were obtained from Guangxi Medical University. All experiments were conducted in accordance with the guidelines of the Animal Committee and with ethics approval from the Guangxi Medical University Animal Care and Use Committee, China (Protocol Number: 2015-11-27). A total of 152 male SD rats with a weight of 180±20 g were used. After anesthesia, 144 randomly selected rats underwent bilateral anterior cruciate ligament transection (ACLT) on the right knee joints to induce OA. Another 8 rats received sham operations (Sham group), in which the articular cavity was opened and sutured with the short anterior cruciate ligament intact. After surgery, all animals were returned to their cages, with the limbs not immobilized. One month after the surgery, the animals were randomly sorted into seven groups (n=24) and were i.a. injected once per week with the following regimens for 8 weeks: SLFNP+HA (1.74 μg Li in 50 μL 10 mg/mL HA), SLFNP alone (1.74 μg Li in 50 μt PBS), LiCl+HA (3.48 μg Li in 50 μL 10 mg/mL HA), LiCl alone (3.48 μg in 50 μL PBS), HA alone (50 μL), and PBS (50 μL). In the sham groups, no other procedures were conducted. The animals in the six groups were sacrificed at 4 and 8 weeks after therapy (n=12).

(17) Serum Lithium Levels

SD rats were intra-articularly (i.a.) injected with HA plus 5 mM SLFNP or 10 mM LiCl (n=3). Blood was collected at 0.5, 1, 2, 4, 12 and 24 h from the eyeballs of rats. Lithium levels in the rat's blood were determined using ICP-MS (Thermo Fishier, USA). For controls, the serum lithium levels in normal SD rats were analyzed.

(18) Macroscopic Observation

After 4 and 8 weeks of treatment, SD rats were sacrificed by intraperitoneal overdose of pentobarbital. Two independent observers who were blinded to the treatment group performed macroscopic evaluation. The observers evaluated the depth of lesions of the articular cartilage on a scale of 0-4 (0=normal-appearing surface, 1=minimal fibrillation or a slight yellow discoloration of the surface, 2=erosion extending into the superficial or middle layers only, 3=erosion extending into the deep layers, and 4=erosion extending to the subchondral bone). The surface area of erosion was calculated with a digital caliper and presented them as mm2, with a higher score indicating greater cartilage damage.

(19) Histological Examination

For the in vivo study, after resection of each femoral head, each specimen was examined and two or three areas were selected from which appeared to be representative of an abnormal process. After fixation in 10% buffered formalin and decalcification with buffered ethylenediaminetetraacetate (EDTA), specimens were embedded in paraffin for histological evaluation. Serial sections (3 μm) were prepared and stained with Hematoxylin Eosin (HE, Nanjingjiancheng, China, Nanjing) and Safranin O-Fast Green (Sigma, USA). Then two independent observers graded the OA lesions on a scale of 0-14 by using the Osteoarthritis Research Society International (OARSI)-modified Mankin criteria. This scale evaluates the severity of OA lesions based on the loss of Safranin 0-fast green staining, cellular changes, invasion of tidemark by blood vessels, and structural changes. The observers based the scoring on the most severe histologic changes within each cartilage section.

(20) Western Blot Analysis

Proteins were extracted from the harvested cartilage using RIPA lysis buffer (Beyotime Institute of Biotechnology, China), denatured for 10 min at 95° C., and cooled on ice for 2 min. Equal amounts of protein samples were loaded per lane and then separated in 10% (v/v) SDS-polyacrylamide gels, and subsequently transferred to a polyvinylidene fluoride (PVDF) membrane (Millipore, Billerica, Mass.). The membranes were blocked with 5% (v/v) milk in Tris-buffered saline containing 0.05% Tween 20 at room temperature for 1 h and then incubated with primary antibodies against MMP-13 (1:200 dilution, Abcam, USA), iNOS (1:40 dilution, Abcam, USA), COX-2 (1:800 dilution, Cell signaling, USA), and β-actin (1:1000 dilution, Proteintech, USA) at 4° C. overnight. After incubated with secondary fluorescence-conjugated goat anti-rabbit IgG for MMP-13, iNOS and COX-2 and goat anti-mouse IgG for β-actin, signals were scanned by Odyssey Infrared Imaging System (LI-COR, USA).

(21) Immunohistochemistry

To analyze the secretion of collagen type II, immunohistochemical staining was used. Cells were washed with PBS and exposed to 3% (v/v) hydrogen peroxide H2O2 to block any endogenous peroxidase activity for 15 min at room temperature. After blocking with normal goat serum for 20 min at room temperature, samples were incubated with primary antibodies of collagen type II (Bioss, China, 1:100) overnight at 4° C. and then incubated again with second antibody and biotin-labeled horse radish peroxidase. For color development, a 3,3'-diaminobenzidine tetrahydrochloride (DAB) kit (Boster, China) was used and counterstained with hematoxylin. Cells were observed and photographed under an inverted phase contrast microscope (Nikon, Japan).

(22) Statistical Analysis

All data are expressed as the means±SD or as the median (scatter grams), and statistical analysis were carried out using one-way analysis of variance (ANOVA) followed by an LSD test if the results were significant or a Mann-Whitney U test (macroscopic score). P<0.05 is statistically significant.

D. REFERENCES

References

Almalik, A. et al. Hyaluronic acid (HA) presentation as a tool to modulate and control the receptor-mediated uptake of HA-coated nanoparticles. *Biomaterials* 34, 5369-5380 (2013).

Altman, R., Manjoo, A., Fierlinger, A., Niazi, F. & Nicholls, M. The mechanism of action for hyaluronic acid treatment in the osteoarthritic knee: a systematic review. *BMC Musculoskelet Disord.* 16, 321 (2015).

Brown, T., Laurent, U. & Fraser, J. Turnover of hyaluronan in synovial joints: elimination of labelled hyaluronan from the knee joint of the rabbit. *Exp. Physiol.* 76, 125-134 (1991). Chevalier, X. et al. Tissue inhibitor of metalloprotease-1 (TIMP-1) serum level may predict progression of hip osteoarthritis. *Osteoarthritis Cartilage* 9, 300-307 (2001).

Cox, S. et al. Collagen degradation by interleukin-1β-stimulated gingival fibroblasts is accompanied by release and activation of multiple matrix metalloproteinases and cysteine proteinases. *Oral Diseases* 12, 34-40 (2006).

Finley, P. R., Warner, M. D. & Peabody, C. A. Clinical relevance of drug-interactions with lithium. *Clin. Pharmacokinet.* 29, 172-191 (1995).

Geddes, J. R. et al. Long-term lithium therapy for bipolar disorder: Systematic review and meta-analysis of randomized controlled trials. *Am. J. Psychiat.* 161, 1517-1517 (2004).

Goldring, M. B. & Otero, M. Inflammation in osteoarthritis. *Curr. Opin. Rheumatol.* 23, 471-478 (2011).

Hui, W. et al. Lithium protects cartilage from cytokine-mediated degradation by reducing collagen-degrading MMP production via inhibition of the P38 mitogen-activated protein kinase pathway. *Rheumatology* 49, 2043-2053 (2010).

Hunter, D. J., Neogi, T. & Hochberg, M. C. Quality of osteoarthritis management and the need for reform in the US. *Arthrit. Care Res.* 63, 31-38 (2011).

LaVan, D. A., McGuire, T. & Langer, R. Small-scale systems for in vivo drug delivery. *Nature Biotechnol.* 21, 1184-1191 (2003).

Lawrence, R. C. et al. Estimates of the prevalence of arthritis and other rheumatic conditions in the United States. *Arthritis Rheum.* 58, 26-35 (2008).

Lewis, A. L. & Illum, L. Formulation strategies for sustained release of proteins. *Therapeutic Delivery* 1, 457-479 (2010).

Marmol, F. Lithium: Bipolar disorder and neurodegenerative diseases Possible cellular mechanisms of the therapeutic effects of lithium. *Prog. Neuro-Psychoph.* 32, 1761-1771 (2008).

Marshall, K. & Chan, A. Arthroscopic anterior cruciate ligament transection induces canine osteoarthritis. *J. Rheumatol.* 23, 338-343 (1996).

Martel-Pelletier, J. et al. Neutral proteases capable of proteoglycan digesting activity in osteoarthritic and normal human articular cartilage. *Arthritis Rheum.* 27, 305-312 (1984).

Minashima, T., Zhang, Y., Lee, Y. & Kirsch, T. Lithium protects against cartilage degradation in osteoarthritis. *Arthritis Rheumatol.* 66, 1228-1236 (2014).

Oruch, R., Elderbi, M. A., Khattab, H. A., Pryme, I. F. & Lund, A. Lithium: A review of pharmacology, clinical uses, and toxicity. *Eur. J Pharmacol.* 740, 464-473 (2014).

Pritzker, K. P. et al. Osteoarthritis cartilage histopathology: grading and staging. Osteoarthritis Cartilage. 14, 13-29 (2006)

Schaafsma, G. Calcium in extracellular fluid: homeostasis. *in Calcium in Human Biology,* 241-259 (Springer, 1988).

Thompson, C. L. et al. Lithium chloride prevents interleukin-1 induced cartilage degradation and loss of mechanical properties. *J. Orthop. Res.* 33, 1552-1559 (2015).

Thompson, C. L. et al. Lithium chloride prevents interleukin-lbeta induced cartilage degradation and loss of mechanical properties. *J. Orthop. Res.* 33, 1552-1559 (2015).

Thompson, C. L., Wiles, A., Poole, C. A. & Knight, M. M. Lithium chloride modulates chondrocyte primary cilia and inhibits Hedgehog signaling. *Faseb J.* 30, 716-726 (2016).

Timmer, R. T. & Sands, J. M. Lithium intoxication. *J. Am. Soc. Nephrol.* 10, 666-674 (1999).

Young, W. Review of lithium effects on brain and blood. *Cell Transplant.* 18, 951-975 (2009).

What is claimed is:

1. A method of treating an inflammatory disease in a subject comprising administering to the subject a particle comprising a lithium salt core and an encapsulating silica shell; wherein the lithium salt core is not a lithium chloride (LiCl) salt core.

2. The method of claim 1, wherein the inflammatory disease is osteoarthritis.

3. The method of claim 1, wherein the composition is administered intra articularly.

4. The method of claim 1, wherein the lithium salt is selected from the group consisting of lithium fluoride (LiF) salt, lithium bromide (LiBr) salt, lithium iodide (LiI) salt, lithium aluminum oxide ($LiAlO_2$) salt, Lithium phosphaste ($Li_3PO_4$), Lithium carbonate ($LiCO_3$) salt, and lithium tantalum oxide ($LiTaO_3$) salt.

5. The method of claim 1, wherein the lithium salt is LiF.

6. The method of claim 5, wherein the concentration of LiF salt comprises 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mM.

7. The method of claim 1, wherein the lithium core further comprises an eluting matrix that releases the Li salt from the matrix over a sustained rate.

8. The method of claim 7, wherein the eluting matrix comprises hyaluronic acid.

9. The method of claim 7, wherein the lithium salt is synthesized in a synthesis matrix comprising a polyethylene glycol (PEG) and ethylene glycol (EG) mixture.

10. The method of claim 9, wherein the PEG:EG ratio is 1:1.

11. The method of claim 1, wherein the lithium core comprises a diameter between about 90 nm and 110 nm.

12. The method of claim 1, wherein the diameter of the lithium core is 50, 55, 60, 65, 70, 75, 80, 85, 90, 95, 100, 105, or 110 nm.

13. The method of claim 1, wherein the encapsulating shell has a thickness of about 20 nm.

14. A method of treating osteoarthritis in a subject comprising administering to the subject a particle comprising a lithium fluoride (LiF) salt core and an encapsulating silica shell; wherein the LiF salt core further comprises a hyaluronic acid eluting matrix that releases the LiF salt from the matrix over a sustained rate.

15. The method of claim 1, wherein the silica shell comprises Tetraethyl orthosilicate.

* * * * *